(12) United States Patent
Gunasekera et al.

(10) Patent No.: US 6,218,419 B1
(45) Date of Patent: Apr. 17, 2001

(54) AMINOIMINOQUINONE AND AMINOQUINONE ALKALOID COMPOUNDS AND METHODS OF USE

(75) Inventors: Sarath P. Gunasekera; Peter J. McCarthy; Ross E. Longley, all of Vero Beach; Shirley A. Pomponi; Amy E. Wright, both of Ft. Pierce, all of FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 09/349,070

(22) Filed: Jul. 8, 1999

Related U.S. Application Data
(60) Provisional application No. 60/092,020, filed on Jul. 8, 1998.

(51) Int. Cl.⁷ .................. A61K 31/404; A61P 35/00; A61P 37/02; C07D 209/04; C07D 209/12

(52) U.S. Cl. .............. 514/415; 514/427; 548/469; 548/494; 548/511; 548/516

(58) Field of Search .................. 514/415, 427; 548/469, 494, 511, 516

(56) References Cited

U.S. PATENT DOCUMENTS

| | | | |
|---|---|---|---|
| 3,265,698 | * | 8/1966 | Allen, Jr. et al. .................. 260/268 |
| 5,028,613 | | 7/1991 | Sun et al. .................. 514/292 |

FOREIGN PATENT DOCUMENTS

| | | |
|---|---|---|
| WO 97/23456 | * 7/1977 | (WO) . |
| 9816502 | 4/1998 | (WO) . |

OTHER PUBLICATIONS

Sun, Hao H., Shinichi Sakemi, Neal Burres, Peter McCarthy (1990) "Isobatzillines A, B, C, and D. Cytotoxic and Antifungal Pyrroloquinoline Alkaloids from the Marine Spone *Batzella* sp." *J. Org. Chem.* 55:4964–4966.

Stierle, Donald B. and D. John Faulkner (1991) "Two New Pyrroloquinoline Alkaloids From The Spone *Damiria* sp." *Journal of Natural Products* 54(4):1131–1133.

Radisky, Derek C., Evette S. Radisky, Louis R. Barrows, Brent R. Copp, Robert A. Kramer, Chris M. Ireland (1993) "Novel Cytotoxic Topoisomerase II Inhibiting Pyrroloiminoquinones from Fijian Sponges of the Genus Zyzzya" *J. Am. Chem. Soc.* 115(5):1632–1638.

Sakemi, Shinichi and Hao H. Sun (1989) "Batzellines A, B, and C. Novel Pyrroloquinoline Alkaloids From the Sponge *Batzella* Sp." *Tetrahedron Lett.* 302:2517–2520.

Faulkner, D. (1998) *J. Nat. Prod. Rep.* 15:113–158.
Faulkner, D. (1997) *J. Nat. Prod. Rep.* 14:259–302.
Faulkner, D. (1996) *J. Nat. Prod. Rep.* 13:75–125.
Faulkner, D. (1995) *J. Nat. Prod. Rep.* 12:223–269.
Faulkner, D. (1994) *J. Nat. Prod. Rep.* 11:355–394.
Faulkner, D. (1993) *J. Nat. Prod. Rep.* 10:497–539.
Faulkner, D. (1992) *J. Nat. Prod. Rep.* 9:323–364.
Faulkner, D. (1991) *J. Nat. Prod. Rep.* 8:97–147.

(List continued on next page.)

*Primary Examiner*—Jane C. Osowecki
(74) *Attorney, Agent, or Firm*—Saliwanchik, Lloyd & Saliwanchik

(57) ABSTRACT

The subject application concerns novel compounds with useful biological properties. For example, these compounds can be used as antinflammatory, anti-proliferative, immunomodulatory, and/or neuroprotective agents. Specific examples of the compounds of the subject invention include Secobatzelline A and Secobatzelline B, which can be isolated from marine sponges.

43 Claims, 2 Drawing Sheets

OTHER PUBLICATIONS

Faulkner, D. (1990) *J. Nat. Prod. Rep.* 7:269–309.
Faulkner, D. (1988) *J. Nat. Prod. Rep.* 5:613–663.
Faulkner, D. (1987) *J. Nat. Prod. Rep.* 4:539–576.
Faulkner, D. (1986) *J. Nat. Prod. Rep.* 3:1–33.
Faulkner, D. (1984) *J. Nat. Prod. Rep.* 1:551–598.
Scheuer, P.D., ed. (1978–1983) In *Marine Natural Products, Chemical and Biological Perspectives,* Academic Press, New York (see entire book, copy not enclosed).
Uemura, D., K. Takahashi, T. Yamamoto et al. (1985) Norhalichondrin A: An Antitumor Polyether Macrolide from a Marine Sponge *J. Am. Chem. Soc.* 107:4796–4798.

* cited by examiner

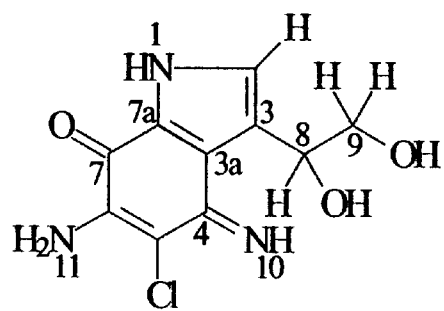
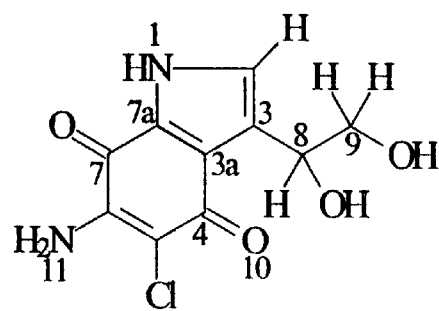
FIG. 1A                    FIG. 1B
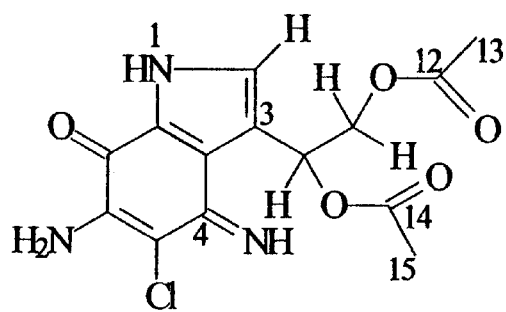
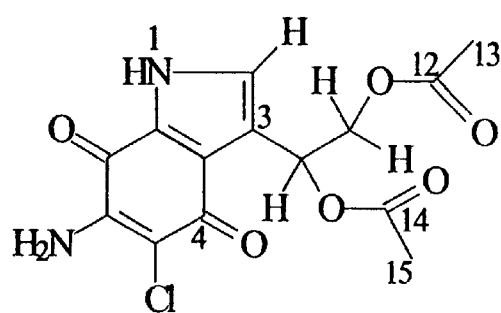
FIG. 1C                    FIG. 1D

US 6,218,419 B1

AMINOIMINOQUINONE AND AMINOQUINONE ALKALOID COMPOUNDS AND METHODS OF USE

CROSS-REFERENCE TO A RELATED APPLICATION

This application claims priority from provisional application U.S. Ser. No. 60/092,020, filed Jul. 8, 1998.

FIELD OF THE INVENTION

The subject invention pertains to novel compounds which can be used as anti-inflammatory, immunomodulatory, neuroprotective, and anti-cancer agents, and to compositions containing such compounds as active ingredients. More particularly, the invention concerns novel biologically active tryptamine-derived aminoquinone and aminoiminoquinone alkaloid compounds, pharmaceutical compositions containing these compounds, uses thereof, and methods of producing the compounds.

BACKGROUND OF THE INVENTION

The prevention and control of inflammation is of prime importance to the maintenance of human and animal health, and much research has been devoted to development of compounds having anti-inflammatory properties. Certain methods and chemical compositions have been developed which aid in inhibiting or controlling inflammation, but additional anti-inflammatory methods and compositions are needed.

Also of great importance to the maintenance of good health is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and anti-cancer compositions are needed.

A further area of great significance in human and animal health care is immunomodulation. Immunomodulator compounds and compositions, are useful for modulating or regulating immunological functions in animals. Immunomodulators may be immunostimulants for building up immunities to, or initiate healing from, certain diseases and disorders. Conversely, immunomodulators may be immunoinhibitors or immunosuppressors for preventing undesirable immune reactions of the body to foreign materials, or to prevent or ameliorate autoimmune reactions or diseases.

Immunomodulators have been found to be useful for treating systemic autoimmune diseases, such as lupus erythematosus and diabetes, as well as immunodeficiency diseases. Further, immunomodulators may be useful for immunotherapy of cancer or to prevent rejections of foreign organs or other tissues in transplants, e.g., kidney, heart, or bone marrow.

Various immunomodulator compounds have been discovered, including FK506, muramylic acid dipeptide derivatives, levamisole, niridazole, oxysuran, flagyl, interferons, interleukins, leukotrienes, corticosteroids, and cyclosporins. Many of these compounds have been found, however, to have undesirable side effects and/or high toxicity. New immunomodulator compounds are therefore needed to provide a wider range of immunomodulator function for specific areas with a minimum of undesirable side effects.

It has been found that some natural products and organisms are potential sources for chemical molecules having useful biological activities. Marine sponges have proved to be such a source, and a number of publications have issued disclosing organic compounds derived from marine sponges. Such publications include Scheuer, P. J., Ed. (1978–1983) *Marine Natural Products, Chemical and Biological Perspectives,* Academic Press, New York; Faulkner, D. (1998)*J. Nat. Prod. Rep.* 15:113–158;(1997)*J. Nat. Prod. Rep.* 14:259–302; (1996)*J. Nat. Prod. Rep.* 13:75–125; (1995)*J. Nat. Prod. Rep.* 12:223–269; (1994)*J. Nat. Prod. Rep.* 11:355–394;(1993)*J. Nat. Prod. Rep.* 10:497–539; (1992)*J. Nat. Prod. Rep.* 9:323–364; (1991)*J. Nat. Prod. Rep.* 8:97–147; (1990)*J. Nat. Prod. Rep.* 7:269–309; (1988) *J. Nat. Prod. Rep.* 5:613–663; (1987)*J. Nat. Prod. Rep.* 4:539–576;(1986)*J. Nat. Prod. Rep.* 3:1–33;(1984)*J. Nat. Prod. Rep.* 1:551–598;and Uemura, D., K. Takahashi, T. Yamamoto, C. Katayama, J. Tanaka, Y. Okumura, Y. Hirata (1985) *J. Am. Chem. Soc.* 107:4796–4798.

Utilizing sponges as a source material and supplemented by novel synthetic production methods, new classes of biologically active compounds and new pharmaceutical compositions have been provided to the art. However, as noted above, there is a great need for additional compounds useful in treating a variety of pathological conditions.

BRIEF SUMMARY OF THE INVENTION

The subject invention concerns tryptamine-derived aminoiminoquinone and aminoquinone alkaloid compounds. Specifically exemplified herein are secobatzellines A and B, as well as compositions containing these compounds. Further aspects of the subject invention pertain to methods of preparation and use of the compounds.

In one preferred embodiment the compounds of the subject invention are useful as inhibitors of biologically important enzymes associated with inflammatory and neurodegenerative processes. The ability of the compounds of the subject invention to inhibit caspase (CPP32) makes these compounds useful in the treatment of a variety of chronic and acute inflammatory diseases including, but not limited to, pancreatitis, rheumatoid arthritis, osteoarthritis, asthma, inflammatory bowel disease, psoriasis and in certain neurological disorders such as Alzheimer's disease.

In a second preferred embodiment, compounds of the subject invention can be used to inhibit pathological cellular proliferation such as that which is associated with cancer. In a further embodiment, the compounds of the subject invention have been found to be useful in immune modulation and, more specifically, immune suppression.

Secobatzelline A (aminoiminoquinone alkaloid) has some structural similarities to the previously known isobatzellines A–D, a class of compounds which has a carbon skeleton of pyrrolo[4,3,2,-de] quinoline derived aminoiminoquinone. However, secobatzelline A possesses an unusual pyrroloaminoiminoquinone with a secoquinoline skeleton system not previously reported from a natural source. Secobatzelline A has shown strong biological activity against the CPP32 enzyme with an $IC_{50}$ value of 0.02 µg/ml and significant anti-cancer activity against P388 murine leukemia ($IC_{50}$=0.06 µg/ml) and A549 human lung adenocarcinoma ($IC_{50}$=0.04 µg/ml). Secobatzellines A and B can be isolated from marine sponges of the genus Batzella as described herein.

BRIEF DESCRIPTION OF THE DRAWINGS

FIG. 1 shows structural formulae of secobatzelline A and B and their diacetates.

DETAILED DISCLOSURE OF THE INVENTION

Figure 2:
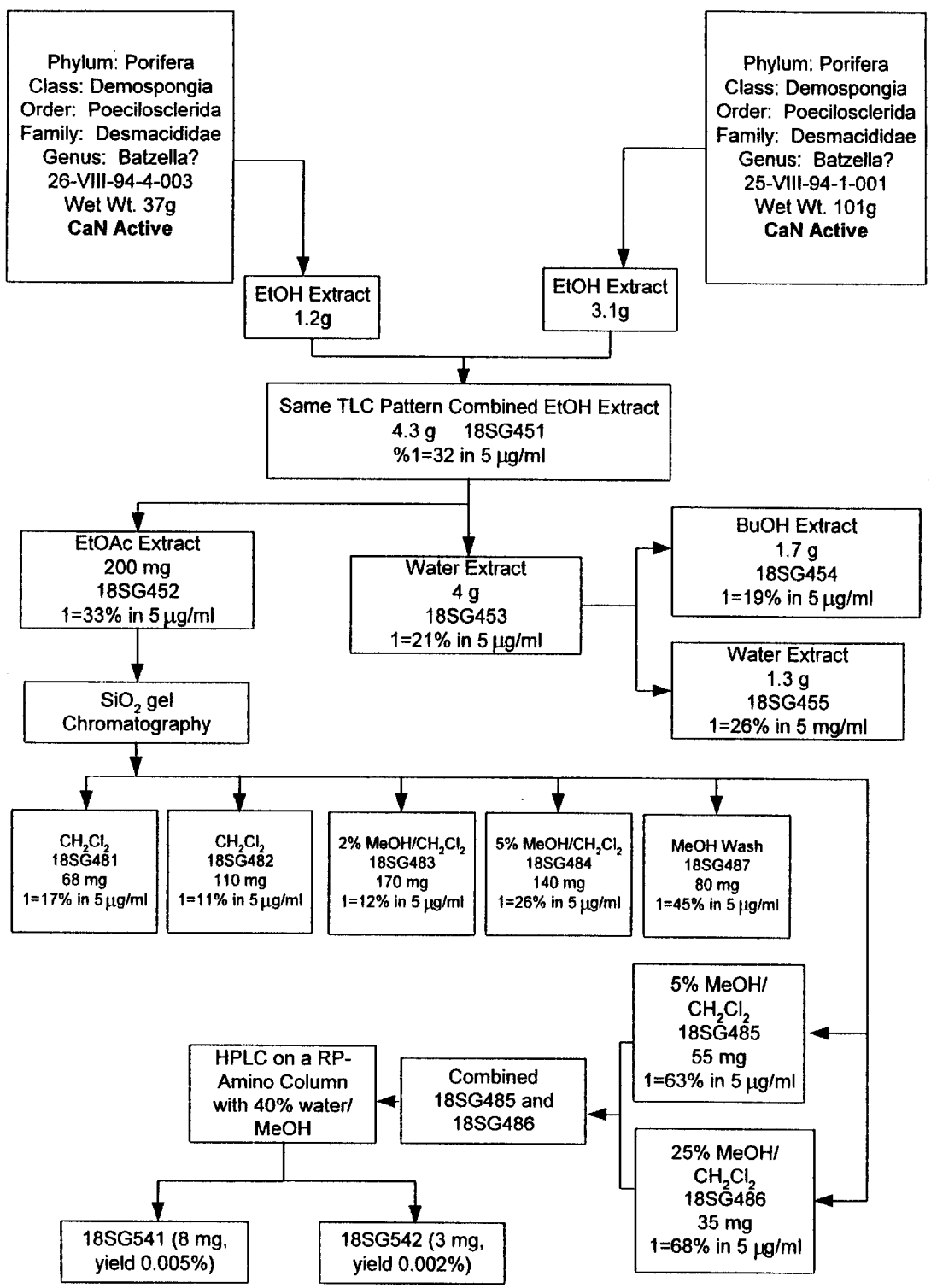
FIG. 2 is a schematic showing the isolation of secobatzellines A and B from a marine sponge source.

The subject invention concerns tryptamine-derived aminoiminoquinone and aminoquinone alkaloid compounds called secobatzellines, and analogs thereof. Further aspects of the subject invention pertain to compositions containing the secobatzellines as well as methods of preparation and use of the compounds. In one embodiment, the compounds of the subject invention can be used as inhibitors of biologically important enzymes. In a specific embodiment, the compounds of the subject invention can be used to inhibit inflammation and/or neurodegeneration.

A specific embodiment of the subject invention pertains to the use of the compounds of the subject invention as caspase inhibitors. Caspase inhibitors are useful in the treatment of a variety of chronic and acute inflammatory diseases such as pancreatitis, rheumatoid arthritis, osteoarthritis, asthma, inflammatory bowel disease, psoriasis and in certain neurological disorders such as Alzheimer's disease.

The caspases, which include CPP32, are a group of at least ten cysteine proteases (also known as interleukin-2 converting enzymes or $ICE_2$), which play a major role in the programmed cell death mechanism known as apoptosis (Patel, T., G. J. Gores, S. H. Kaufmann [1996] *FASEB* 10:587–597). These enzymes are the mammalian homologs of the ced-3 gene product that modulates apoptotic processes in the nematode *Caenorhabditis elegans* (Schwartz, L. M., C. E. Milligan [1996] *Trends Neursci* 19:555–562). Mutations in ced-3 prevent apoptosis during normal development of the nematode and in mammals, inhibitors of caspase-3 (CPP32) have been shown to prevent apoptotic mediated death in a number of cell lines and in various tissues (Schwartz, L. M., C. E. Milligan [1996] *Trends Neursci* 19:555–562; Milligan, C. E., D. Prevette, H. Yaginuma, S. Homma, C. Cardwell, L. C. Fritz, K. J. Tomaselli, R. W. Oppenheim, L. M. Schwartz [1995] *Neuron* 15:385–393).

Apoptotic mechanisms play important roles in the normal development of the immune repertoire and in tissue remodeling during embryonic development in both vertebrates and invertebrates (Kerr, J. F. R., A. H. Wyllie, A. R. Currie [1972] *Br. J. Cancer* 26:239–257). However, aberrant apoptosis has been implicated in a number of experimental and human disease states. For example, in acute CNS injury following hypoxic-ischemic insult in mice, there is evidence that caspase-induced apoptosis is the prime factor in neuronal destruction (Hara, H., R. M. Friedlander, V. Gagliardini, C. Ayata, K. Fink, Z. Huang, M. Shimizu-Sasamata, J. Yuan, M. A. Moskowitz [1997] *Proc. Natl. Acad. Sci. USA* 94:2007–2012). In addition, caspases have been implicated in chronic neurodegenerative disorders, which would suggest their role in the pathogenesis of amyotrophic lateral sclerosis (ALS) and in Alzheimer's disease (Friedlander, R. M., R. H. Brown, V. Gagliardini, J. Wang, J. Yuan [1997] *Nature* 388:31; Kim, T.-W., W. H. Pettingell, Y.-K. Jung, D. M. Kovacs, R. E. Tanzi [1997] *Science* 277:373–376). Caspase-3 (CPP32) has also been shown to be involved in the stimulation of IL-8 secretion of synoviocytes in rheumatoid arthritis which serves to increase joint inflammation and progress of the disease (Sekine, C., H. Yagita, T. Kobata, T. Hasunuma, K. Nishioka, K. Okumura [1996] *Biochem. Biophys. Res. Commun.* 228:14–20). Therefore, inhibitors of caspase enzymatic activities can be used to prevent or reduce the pathological damage induced by caspase mediated apoptotic events.

In a further specific embodiment, the compounds of the subject invention can be used to treat pathological cellular proliferation in humans or other animals. Thus, the compositions and methods of the subject invention can be used in the treatment of an animal (including humans) hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, or lung tumors, as well as human leukemia or melanoma cells. The capability for achieving anticancer activity exhibited by the subject compounds would lead a person of ordinary skill in the art to recognize the applicability of the subject compounds, compositions, and methods to additional types of cancer as described herein.

In accordance with the subject invention, methods for inhibiting tumors in a host include contacting tumor cells with an effective amount of the new pharmaceutical compositions of the invention. The tumor cells inhibited by the invention are those which are susceptible to the subject compounds described herein or compositions comprising those compounds.

The subject invention further pertains to use of the subject compounds as immunomodulators. In one embodiment, the subject invention pertains to the immunosuppressive use of the subject compounds. These compounds can be used to reduce, suppress, inhibit, or prevent unwanted immune responses. Advantageously, this immunosuppression can be achieved without cytotoxicity. Thus, the compounds of the subject invention are useful for treatments of humans or animals requiring immunosuppression. Examples of conditions for which immunosuppression is desired include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents.

In a specific embodiment, the compounds of the subject invention have been found to inhibit calcineurin. Calcineurin is an enzyme and a member of the serine/threonine phosphatase family of cell signal transduction proteins. Calcineurin is recognized to be a principal signaling molecule that regulates immune responsiveness. Calcineurin's phosphatase activity is inhibited through an association with a complex formed by the immunosuppressant FK506 and an intracellular protein, FKBP-12 (FK506 Binding Protein), which results in immunosuppression. Therefore, inhibitors of calcineurin, such as the compounds of the subject invention, can be used to inhibit immune responsiveness through inhibition of calcineurin associated phosphatase activity. Inhibition of immune responsiveness by the subject compounds is useful for the treatment of conditions including systemic autoimmune disease, immunodeficiency diseases, immunotherapy of cancer or to prevent rejections of foreign organs or other tissues in transplants (i.e., kidney, heart, lungs, colon, liver, or bone marrow).

Secobatzelline A (aminoiminoquinone) and secobatzelline B (aminoquinone), isolated from marine sponges, are shown in FIG. 1 as Structures 1 and 2, respectively. Acetylation of secobatzelline A gives the diacetate shown as Structure 3 in FIG. 1. The acetylation of secobatzelline B yields the diacetate shown as Structure 4 in FIG. 1.

The marine sponges, from which the secobatzelline compounds of the subject invention can be isolated, can be collected from the Bahamas, North Bimini, west of Alice Town (latitude 25° 44, 288' N; longitude 79° 18.981' W). For example, a sample was obtained at the depth of 455 feet. Habitat: 10 degree sand slope with small isolated rocks. Substrate: Rock. Morphology: thick encrusting cushion with papillae. External and internal color: black. Another collection site is western Great Bahama Bank (latitude 25° 23;921' N; longitude 79° 14.104' W). Another sample was collected at 500 feet. Habitat: 60 degree sand and rubble slope. Substrate: rubble. Morphology: thick encrusting cushion with papillae. External color: dark brown and internal color: brown.

Detailed Taxonomic Description

Phylum: Porifera
Class: Demospongiae
Order: Poecilosclerida
Family: Desmacididae
Genus: Batzella
Species—undescribed This sponge has been assigned to the genus Batzella, as described and discussed by Van Socst et al., 1996, pp 95–97 (Bulletin de l'Institut Royal des Sciences Naturelles de Belgique, Biologie, 66 suppl: 89–101). The sponge has a detachable ectosome and a spicule skeleton of strongyles of one size category. Some of the strongyles have malformed tips. The sponge incorporates sediment into its skeleton. There are numerous papillae scattered over the surface of the sponge. The sponge is dark brown to black when alive, brown when preserved in ethanol. Taxonomic reference samples have been deposited in the Harbor Branch Oceanographic Institution Museum, catalog numbers 003:00930 (25-VIII-94-1-001) and 003:00931 (26-VIII-94-4-003). Voucher specimens are preserved in 70% ethanol with an expected shelf life of at least 30 years and are accessible to those skilled in the art for, for example, taxonomic identification purposes.

Compounds of the subject invention can be represented by the following general formula:

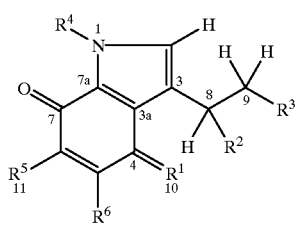

wherein $R^1$ is NH or O;
$R^2$ is OZ;
$R^3$ is OZ;
$R^4$ is H or R;
$R^5$ is $NH_2$, $NR_2$, or OZ; and
$R^6$ is H or X;
wherein Z is selected from the group consisting of H, R, COR, mesyl, tosyl, glutamyl, succinyl, and malonyl;

R is selected from the group consisting of C1 to C8 alkyl, phenyl, and benzyl; and X is Cl, Br, or I.

Specifically exemplified herein are compounds having the following structures:

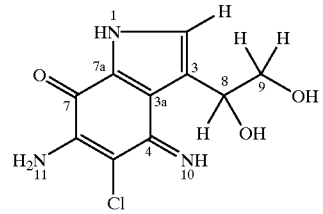

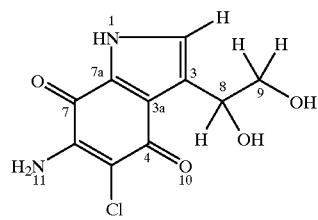

Structure 1 is secobatzelline A and Structure 2 is secobatzelline B. Included within the scope of the subject invention are salts of the protonated Structures 1 and 2. These salts may be, for example, $Cl^-$; $Br^-$; $CH_3COO^-$; $HSO_3O^-$, citrate, tartrate or oxalate.

Acylation (OH→OCOR) can be achieved by, for example, treating a compound with a mixture of alkyl anhydride and pyridine (1:1) at room temperature overnight or maintaining at 60° C. for ~4 hours.

Alkylation (NH→$NR^4$ or $NH_2$→$NR^5$) can be achieved by, for example, refluxing a compound in dry acetone with RI (alkyliodide) in the presence of anhydrous $K_2CO_3$.

Hydrogenolysis (Cl→H) can be achieved by shaking a compound in ethanol in an atmosphere of $H_2$ at 50 psi in the presence of the catalyst 10% vanadium on activated carbon.

The conversion of ($R^5$=$NH_2$→OH) can be achieved by diazotiation of a compound at 5° C. followed by warming the diazotized product for a few hours in the presence of ethanol.

A preferred embodiment is secobatzelline A (Structure 1) and its diacetate (Structure 3):

Secobatzelline A (1) $R^1$=NH, $R^2$=OH, $R^3$=OH, $R^4$=H, $R^5$=$NH_2$, $R^6$=Cl Diacetate (3) $R^1$=NH, $R^2$=OCOR, $R^3$=OCOR, $R^4$=H, $R^5$=$NH_2$, $R^6$=Cl A second preferred embodiment is secobatzelline B (Structure 2) and its diacetate (Structure 4):

Secobatzelline B (2) $R^1$=O, $R^2$=OH, $R^3$=OH, $R^4$=H, $R^5$=$NH_2$, $R^6$=Cl Diacetate (4) $R^1$=O, $R^2$=OCOR, $R^3$=OCOR, $R^4$=H, $R^5$=$NH_2$, $R^6$=Cl Further preferred embodiments include compounds where the R groups are, independently, selected from the groups consisting of C1→C8 alkyl and phenyl; Z is selected from mesyl, tosyl, glutamyl, succinyl and malonyl; and X is selected from Cl, Br, or I. Specific analogs of the subject invention are as follows:

| | |
|---|---|
| Analog (5) | $R^1$ = NH, $R^2$ = OH, $R^3$ = OCOR, $R^4$ = H, $R^5$ = NH$_2$, $R^6$ = X |
| Analog (6) | $R^1$ = NH, $R^2$ = OH, $R^3$ = OZ, $R^4$ = H, $R^5$ = NH$_2$, $R^6$ = X |
| Analog (7) | $R^1$ = NH, $R^2$ = OCOR, $R^3$ = OH, $R^4$ = H, $R^5$ = NH$_2$, $R^6$ = X |
| Analog (8) | $R^1$ = NH, $R^2$ = OZ, $R^3$ = OH, $R^4$ = H, $R^5$ = NH$_2$, $R^6$ = X |
| Analog (9) | $R^1$ = O, $R^2$ = OH, $R^3$ = OCOR, $R^4$ = H, $R^5$ = NH$_2$, $R^6$ = X |
| Analog (10) | $R^1$ = O, $R^2$ = OH, $R^3$ = OZ, $R^4$ = H, $R^5$ = NH$_2$, $R^6$ = X |
| Analog (11) | $R^1$ = O, $R^2$ = OCOR, $R^3$ = OH, $R^4$ = H, $R^5$ = NH$_2$, $R^6$ = X |
| Analog (12) | $R^1$ = O, $R^2$ = OZ, $R^3$ = OH, $R^4$ = H, $R^5$ = NH$_2$, $R^6$ = X |
| Analog (13) | $R^1$ = NH, $R^2$ = OH, $R^3$ = OH, $R^4$ = R, $R^5$ = NH$_2$, $R^6$ = X |
| Analog (14) | $R^1$ = O, $R^2$ = OH, $R^3$ = OH, $R^4$ = R, $R^5$ = NH$_2$, $R^6$ = X |
| Analog (15) | $R^1$ = NH, $R^2$ = OH, $R^3$ = OH, $R^4$ = H, $R^5$ = NR$_2$, $R^6$ = X |
| Analog (16) | $R^1$ = O, $R^2$ = OH, $R^3$ = OH, $R^4$ = H, $R^5$ = NR$_2$, $R^6$ = X |
| Analog (17) | $R^1$ = NH, $R^2$ = OH, $R^3$ = OH, $R^4$ = R, $R^5$ = NR$_2$, $R^6$ = X |
| Analog (18) | $R^1$ = O, $R^2$ = OH, $R^3$ = OH, $R^4$ = R, $R^5$ = NR$_2$, $R^6$ = X |
| Analog (19) | $R^1$ = NH, $R^2$ = OCOR, $R^3$ = OCOR, $R^4$ = R, $R^5$ = NH$_2$, $R^6$ = X |
| Analog (20) | $R^1$ = NH, $R^2$ = OZ, $R^3$ = OZ, $R^4$ = R, $R^5$ = NH$_2$, $R^6$ = X |
| Analog (21) | $R^1$ = O, $R^2$ = OCOR, $R^3$ = OCOR, $R^4$ = R, $R^5$ = NH$_2$, $R^6$ = X |
| Analog (22) | $R^1$ = O, $R^2$ = OZ, $R^3$ = OZ, $R^4$ = R, $R^5$ = NH$_2$, $R^6$ = X |
| Analog (23) | $R^1$ = NH, $R^2$ = OCOR, $R^3$ = OH, $R^4$ = H, $R^5$ = NR$_2$, $R^6$ = X |
| Analog (24) | $R^1$ = NH, $R^2$ = OZ, $R^3$ = OH, $R^4$ = H, $R^5$ = NR$_2$, $R^6$ = X |
| Analog (25) | $R^1$ = O, $R^2$ = OCOR, $R^3$ = OH, $R^4$ = H, $R^5$ = NR$_2$, $R^6$ = X |
| Analog (26) | $R^1$ = O, $R^2$ = OZ, $R^3$ = OH, $R^4$ = H, $R^5$ = NR$_2$, $R^6$ = X |
| Analog (27) | $R^1$ = NH, $R^2$ = OH, $R^3$ = OCOR, $R^4$ = R, $R^5$ = NR$_2$, $R^6$ = X |
| Analog (28) | $R^1$ = NH, $R^2$ = OH, $R^3$ = OZ, $R^4$ = R, $R^5$ = NR$_2$, $R^6$ = X |
| Analog (29) | $R^1$ = O, $R^2$ = OH, $R^3$ = OCOR, $R^4$ = R, $R^5$ = NR$_2$, $R^6$ = X |
| Analog (30) | $R^1$ = O, $R^2$ = OH, $R^3$ = OZ, $R^4$ = R, $R^5$ = NR$_2$, $R^6$ = X |
| Analog (31) | $R^1$ = NH, $R^2$ = OCOR, $R^3$ = OCOR, $R^4$ = H, $R^5$ = NH$_2$, $R^6$ = H |
| Analog (32) | $R^1$ = NH, $R^2$ = OZ, $R^3$ = OZ, $R^4$ = H, $R^5$ = NH$_2$, $R^6$ = H |
| Analog (33) | $R^1$ = O, $R^2$ = OCOR, $R^3$ = OCOR, $R^4$ = H, $R^5$ = NH$_2$, $R^6$ = H |
| Analog (34) | $R^1$ = O, $R^2$ = OZ, $R^3$ = OZ, $R^4$ = H, $R^5$ = NH$_2$, $R^6$ = H |
| Analog (35) | $R^1$ = NH, $R^2$ = OH, $R^3$ = OCOR, $R^4$ = H, $R^5$ = NH$_2$, $R^6$ = H |
| Analog (36) | $R^1$ = NH, $R^2$ = OH, $R^3$ = OZ, $R^4$ = H, $R^5$ = NH$_2$, $R^6$ = H |
| Analog (37) | $R^1$ = NH, $R^2$ = OCOR, $R^3$ = OH, $R^4$ = H, $R^5$ = NH$_2$, $R^6$ = H |
| Analog (38) | $R^1$ = NH, $R^2$ = OZ, $R^3$ = OH, $R^4$ = H, $R^5$ = NH$_2$, $R^6$ = H |
| Analog (39) | $R^1$ = O, $R^2$ = OH, $R^3$ = OCOR, $R^4$ = H, $R^5$ = NH$_2$, $R^6$ = H |
| Analog (40) | $R^1$ = O, $R^2$ = OH, $R^3$ = OZ, $R^4$ = H, $R^5$ = NH$_2$, $R^6$ = H |
| Analog (41) | $R^1$ = O, $R^2$ = OCOR, $R^3$ = OH, $R^4$ = H, $R^5$ = NH$_2$, $R^6$ = H |
| Analog (42) | $R^1$ = O, $R^2$ = OZ, $R^3$ = OH, $R^4$ = H, $R^5$ = NH$_2$, $R^6$ = H |
| Analog (43) | $R^1$ = NH, $R^2$ = OH, $R^3$ = OH, $R^4$ = R, $R^5$ = NH$_2$, $R^6$ = H |
| Analog (44) | $R^1$ = O, $R^2$ = OH, $R^3$ = OH, $R^4$ = R, $R^5$ = NH$_2$, $R^6$ = H |
| Analog (45) | $R^1$ = NH, $R^2$ = OH, $R^3$ = OH, $R^4$ = H, $R^5$ = NR$_2$, $R^6$ = H |
| Analog (46) | $R^1$ = O, $R^2$ = OH, $R^3$ = OH, $R^4$ = H, $R^5$ = NR$_2$, $R^6$ = H |
| Analog (47) | $R^1$ = NH, $R^2$ = OH, $R^3$ = OH, $R^4$ = R, $R^5$ = NR$_2$, $R^6$ = H |
| Analog (48) | $R^1$ = O, $R^2$ = OH, $R^3$ = OH, $R^4$ = R, $R^5$ = NR$_2$, $R^6$ = H |
| Analog (49) | $R^1$ = NH, $R^2$ = OCOR, $R^3$ = OCOR, $R^4$ = R, $R^5$ = NH$_2$, $R^6$ = H |
| Analog (50) | $R^1$ = NH, $R^2$ = OZ, $R^3$ = OZ, $R^4$ = R, $R^5$ = NH$_2$, $R^6$ = H |
| Analog (51) | $R^1$ = O, $R^2$ = OCOR, $R^3$ = OCOR, $R^4$ = R, $R^5$ = NH$_2$, $R^6$ = H |
| Analog (52) | $R^1$ = O, $R^2$ = OZ, $R^3$ = OZ, $R^4$ = R, $R^5$ = NH$_2$, $R^6$ = H |
| Analog (53) | $R^1$ = NH, $R^2$ = OCOR, $R^3$ = OH, $R^4$ = H, $R^5$ = NR$_2$, $R^6$ = H |
| Analog (54) | $R^1$ = NH, $R^2$ = OZ, $R^3$ = OH, $R^4$ = H, $R^5$ = NR$_2$, $R^6$ = H |
| Analog (55) | $R^1$ = O, $R^2$ = OCOR, $R^3$ = OH, $R^4$ = H, $R^5$ = NR$_2$, $R^6$ = H |
| Analog (56) | $R^1$ = O, $R^2$ = OZ, $R^3$ = OH, $R^4$ = H, $R^5$ = NR$_2$, $R^6$ = H |
| Analog (57) | $R^1$ = NH, $R^2$ = OH, $R^3$ = OCOR, $R^4$ = R, $R^5$ = NR$_2$, $R^6$ = H |
| Analog (58) | $R^1$ = NH, $R^2$ = OH, $R^3$ = OZ, $R^4$ = R, $R^5$ = NR$_2$, $R^6$ = H |
| Analog (59) | $R^1$ = O, $R^2$ = OH, $R^3$ = OCOR, $R^4$ = R, $R^5$ = NR$_2$, $R^6$ = H |
| Analog (60) | $R^1$ = O, $R^2$ = OH, $R^3$ = OZ, $R^4$ = R, $R^5$ = NR$_2$, $R^6$ = H |
| Analog (61) | $R^1$ = NH, $R^2$ = OCOR, $R^3$ = OCOR, $R^4$ = H, $R^5$ = OH, $R^6$ = X |
| Analog (62) | $R^1$ = NH, $R^2$ = OZ, $R^3$ = OZ, $R^4$ = H, $R^5$ = OH, $R^6$ = X |
| Analog (63) | $R^1$ = NH, $R^2$ = OCOR, $R^3$ = OCOR, $R^4$ = H, $R^5$ = OCOR, $R^6$ = X |
| Analog (64) | $R^1$ = NH, $R^2$ = OZ, $R^3$ = OZ, $R^4$ = H, $R^5$ = OZ, $R^6$ = X |
| Analog (65) | $R^1$ = O, $R^2$ = OCOR, $R^3$ = OCOR, $R^4$ = H, $R^5$ = OH, $R^6$ = X |
| Analog (66) | $R^1$ = O, $R^2$ = OZ, $R^3$ = OZ, $R^4$ = H, $R^5$ = OH, $R^6$ = X |
| Analog (67) | $R^1$ = O, $R^2$ = OCOR, $R^3$ = OCOR, $R^4$ = H, $R^5$ = OCOR, $R^6$ = X |
| Analog (68) | $R^1$ = O, $R^2$ = OZ, $R^3$ = OZ, $R^4$ = H, $R^5$ = OZ, $R^6$ = X |
| Analog (69) | $R^1$ = NH, $R^2$ = OH, $R^3$ = OH, $R^4$ = H, $R^5$ = OH, $R^6$ = X |
| Analog (70) | $R^1$ = O, $R^2$ = OH, $R^3$ = OH, $R^4$ = H, $R^5$ = OH, $R^6$ = X |
| Analog (71) | $R^1$ = NH, $R^2$ = OH, $R^3$ = OH, $R^4$ = R, $R^5$ = OH, $R^6$ = X |
| Analog (72) | $R^1$ = O, $R^2$ = OH, $R^3$ = OH, $R^4$ = R, $R^5$ = OH, $R^6$ = X |
| Analog (73) | $R^1$ = NH, $R^2$ = OCOR, $R^3$ = OCOR, $R^4$ = R, $R^5$ = OH, $R^6$ = X |
| Analog (74) | $R^1$ = NH, $R^2$ = OZ, $R^3$ = OZ, $R^4$ = R, $R^5$ = OH, $R^6$ = X |
| Analog (75) | $R^1$ = NH, $R^2$ = OCOR, $R^3$ = OCOR, $R^4$ = R, $R^5$ = OCOR, $R^6$ = X |
| Analog (76) | $R^1$ = NH, $R^2$ = OZ, $R^3$ = OZ, $R^4$ = R, $R^5$ = OZ, $R^6$ = X |
| Analog (77) | $R^1$ = O, $R^2$ = OCOR, $R^3$ = OCOR, $R^4$ = R, $R^5$ = OH$_2$, $R^6$ = X |
| Analog (78) | $R^1$ = O, $R^2$ = OZ, $R^3$ = OZ, $R^4$ = R, $R^5$ = OH$_2$, $R^6$ = X |
| Analog (79) | $R^1$ = O, $R^2$ = OCOR, $R^3$ = OCOR, $R^4$ = R, $R^5$ = OCOR, $R^6$ = X |
| Analog (80) | $R^1$ = O, $R^2$ = OZ, $R^3$ = OZ, $R^4$ = R, $R^5$ = OZ, $R^6$ = X |
| Analog (81) | $R^1$ = NH, $R^2$ = OCOR, $R^3$ = OH, $R^4$ = H, $R^5$ = OH, $R^6$ = X |
| Analog (82) | $R^1$ = NH, $R^2$ = OZ, $R^3$ = OH, $R^4$ = H, $R^5$ = OH, $R^6$ = X |
| Analog (83) | $R^1$ = O, $R^2$ = OCOR, $R^3$ = OH, $R^4$ = H, $R^5$ = OH, $R^6$ = X |

-continued

| | |
|---|---|
| Analog (84) | $R^1 = O, R^2 = OZ, R^3 = OH, R^4 = H, R^5 = OH, R^6 = X$ |
| Analog (85) | $R^1 = NH, R^2 = OH, R^3 = OCOR, R^4 = R, R^5 = OH, R^6 = X$ |
| Analog (86) | $R^1 = NH, R^2 = OH, R^3 = OZ, R^4 = R, R^5 = OH, R^6 = X$ |
| Analog (87) | $R^1 = O, R^2 = OH, R^3 = OCOR, R^4 = R, R^5 = OH, R^6 = X$ |
| Analog (88) | $R^1 = O, R^2 = OH, R^3 = OZ, R^4 = R, R^5 = OH, R^6 = X$ |
| Analog (89) | $R^1 = NH, R^2 = OCOR, R^3 = OCOR, R^4 = H, R^5 = OH, R^6 = H$ |
| Analog (90) | $R^1 = NH, R^2 = OZ, R^3 = OZ, R^4 = H, R^5 = OH, R^6 = H$ |
| Analog (91) | $R^1 = NH, R^2 = OCOR, R^3 = OCOR, R^4 = H, R^5 = OCOR, R^6 = H$ |
| Analog (92) | $R^1 = NH, R^2 = OZ, R^3 = OZ, R^4 = H, R^5 = OZ, R^6 = H$ |
| Analog (93) | $R^1 = O, R^2 = OCOR, R^3 = OCOR, R^4 = H, R^5 = OH, R^6 = H$ |
| Analog (94) | $R^1 = O, R^2 = OZ, R^3 = OZ, R^4 = H, R^5 = OH, R^6 = H$ |
| Analog (95) | $R^1 = O, R^2 = OCOR, R^3 = OCOR, R^4 = H, R^5 = OCOR, R^6 = H$ |
| Analog (96) | $R^1 = O, R^2 = OZ, R^3 = OZ, R^4 = H, R^5 = OZ, R^6 = H$ |
| Analog (97) | $R^1 = NH, R^2 = OH, R^3 = OH, R^4 = H, R^5 = OH, R^6 = H$ |
| Analog (98) | $R^1 = O, R^2 = OH, R^3 = OH, R^4 = H, R^5 = OH, R^6 = H$ |
| Analog (99) | $R^1 = NH, R^2 = OH, R^3 = OH, R^4 = R, R^5 = OH, R^6 = H$ |
| Analog (100) | $R^1 = O, R^2 = OH, R^3 = OH, R^4 = R, R^5 = OH, R^6 = H$ |
| Analog (101) | $R^1 = NH, R^2 = OCOR, R^3 = OCOR, R^4 = R, R^5 = OH, R^6 = H$ |
| Analog (102) | $R^1 = NH, R^2 = OZ, R^3 = OZ, R^4 = R, R^5 = OH, R^6 = H$ |
| Analog (103) | $R^1 = NH, R^2 = OCOR, R^3 = OCOR, R^4 = R, R^5 = OCOR, R^6 = H$ |
| Analog (104) | $R^1 = NH, R^2 = OZ, R^3 = OZ, R^4 = R, R^5 = OZ, R^6 = H$ |
| Analog (105) | $R^1 = O, R^2 = OCOR, R^3 = OCOR, R^4 = R, R^5 = OH_2, R^6 = H$ |
| Analog (106) | $R^1 = O, R^2 = OZ, R^3 = OZ, R^4 = R, R^5 = OH_2, R^6 = H$ |
| Analog (107) | $R^1 = O, R^2 = OCOR, R^3 = OCOR, R^4 = R, R^5 = OCOR, R^6 = H$ |
| Analog (108) | $R^1 = O, R^2 = OZ, R^3 = OZ, R^4 = R, R^5 = OZ, R^6 = H$ |
| Analog (109) | $R^1 = NH, R^2 = OCOR, R^3 = OH, R^4 = H, R^5 = OH, R^6 = H$ |
| Analog (110) | $R^1 = NH, R^2 = OZ, R^3 = OH, R^4 = H, R^5 = OH, R^6 = H$ |
| Analog (111) | $R^1 = O, R^2 = OCOR, R^3 = OH, R^4 = H, R^5 = OH, R^6 = H$ |
| Analog (112) | $R^1 = O, R^2 = OZ, R^3 = OH, R^4 = H, R^5 = OH, R^6 = H$ |
| Analog (113) | $R^1 = NH, R^2 = OH, R^3 = OCOR, R^4 = R, R^5 = OH, R^6 = H$ |
| Analog (114) | $R^1 = NH, R^2 = OH, R^3 = OZ, R^4 = R, R^5 = OH, R^6 = H$ |
| Analog (115) | $R^1 = O, R^2 = OH, R^3 = OCOR, R^4 = R, R^5 = OH, R^6 = H$ |
| Analog (116) | $R^1 = O, R^2 = OH, R^3 = OZ, R^4 = R, R^5 = OH, R^6 = H$ |

Materials and Methods

P388 and A549 in Vitro Anti-tumor Testing

P388 cells can be obtained from the National Cancer Institute, Bethesda, Md., and A549 cells can be obtained from American Type Culture Collection, Rockville, Md. All cell lines are maintained in Roswell Park Memorial Institute (RPMI) medium 1640 supplemented with 10% bovine calf serum. All cell lines are cultured in plastic tissue culture flasks and kept in an incubator at 37° C. in humidified air containing 5% $CO_2$. Prior to testing, antibiotic-free stock cultures of each of the cell lines are subcultured to $10^6$ cells/ml by dilution in fresh growth medium at 2 to 3 day intervals.

To assess the antiproliferative effects of agents against the P388 cell line, 200 µl cultures (96 well tissue culture plates, Nunc, Denmark) are established at $1 \times 10^5$ cells/ml in drug-free medium or medium containing the test agent at 10.0, 1.0, 0.10 and 0.010 µg/ml. The solvent for all dilutions is ethanol. All experimental cultures are initiated in medium containing Gentamycin sulfate (50 µg/ml; Schering Corporation, Kenilworth, N.J.). After 48-hr exposure, P388 cells are enumerated using 3-[4,5-Dimethylthiazol-2-yl]-2, 5-diphenyltetrazolium bromide (MTT) as described below.

Similar procedures are utilized for A549 cells which require an additional 48 hr exposure prior to MTT addition. Results are expressed as percent inhibition compared to the negative (no drug) control. Positive drug controls are included to monitor drug sensitivity of each of the cell lines. These include varying dilutions of 5-fluorouracil, adriamycin, methotrexate and vinblastine.

To quantitate the effects on cell proliferation and resulting $IC_{50}$ values, 75 µl of warm growth media containing 5 mg/ml MTT is added to each well, cultures are returned to the incubator, and left undisturbed for 90 minutes. To spectrophotometrically quantitate formation of reduced formazan, plates are centrifuged (900×g. 5 minutes), culture fluids removed by aspiration, and 200 µl of acidified isopropanol (2 ml concentrated HCl/liter isopropanol) added per well. The absorbance of the resulting solutions is measured at 570 nm with a plate reader (MR700 Microplate Reader, Dynatech Laboratories, Chantilly, Va.). The absorbance of tests wells is divided by the absorbance of drug-free wells, and the concentration of agent that results in 50% of the absorbance of untreated cultures ($IC_{50}$) is determined by linear regression of logit-transformed data. A linear relationship between tumor cell number and formazan production has been routinely observed over the range of cell densities observed in these experiments. The four standard drug controls (indicated above) are included in each assay as a check to monitor the drug sensitivity of each of the cell lines and $IC_{50}$ values are determined for each drug-cell combination.

Two-Way Mixed Lymphocyte Reaction (MLR) and Lymphocyte Viability (LCV) Testing

These assays measure the ability of the extracts/pure compounds to inhibit allogeneic immune responsiveness (MLR) and to affect the viability of unstimulated lymphocytes. These general methods are described in the following: Longley, R. E., D. Caddigan, D. Harmody, M. Gunasekera and S. P. Gunasekera (1991) *Transplantation* 52: 650–656.

EL-4 Adherence Testing

This assay is based on the properties of extracts/pure compounds which serve as protein kinase C (PKC) active agents to either induce or inhibit the adherence of EL-4.IL-2 murine lymphoma cells to plastic surfaces. The general methodology of this assay is described in detail in the following: Longley, R. E. and D. Harmody (1991) *J. Antibiotics* 44:93–102.

Enzyme Assays

Each of the following assays were performed using either a Tecan 8051 or a Tecan Megaflex automated liquid handling system. Extracts of marine organisms were tested at 5 µg/ml for all assays except DPP IV and LAR which were tested at 50 μg/ml. The inhibition of enzyme activity found in the presence of extract was compared to that of an uninhibited control. Extracts which inhibited the enzyme>50% were retested in triplicate to confirm activity.

(i) CD45

CD45 was prepared as a membrane fraction from Jurkat cells (clone E6-1). Cells were grown in RPMI-1640 medium supplemented with 10% fetal bovine serum and L-glutamine, lysed in hypotonic lysis buffer (25 mM Tris-HCI, 25 mM sucrose, 0.1 mM EDTA, 5 mM $MgCl_2$, 5 mM dithiothreitol, 1 mM phenylmethane sulfonyl fluoride and 10 μg/ml leupeptin, pH 7.5) and centrifuged at 500×g for 5 minutes. The supernatant was then centrifuged at 100,000×g for 1 hr. The pellet, containing CD45, was resuspended in assay buffer (100 mM sodium acetate, 1 mM EDTA, pH 6.0) and stored at −80° C.

The assay was based on that described by Imoto et al. (Imotok, M. H., H. Kakeya, T. Sawa, C. Hayashi, M. Hamada, T. Takeuchi and K. Umezawa [1993] "Dephostin, a novel protein tyrosine phosphatase inhibitor produced by Streptomyces I. Taxonomy, isolation and characterization"*J. Antibiotics* 46:1342–1346) and was performed in a total volume of 50 μl. The CD45 membrane suspension (1 μg protein/well) was incubated in assay buffer at 37° C. with 2.5 mM o-phosphotyrosine as substrate. Test samples were included as required. The reaction was terminated by the addition of 5% $HCIO_4$ (150 μl). Liberated inorganic phosphate was measured by the change in absorbance at 620 nm following the addition of 50 μl of color reagent (6N $H_2SO_4$, 1 mg/ml malachite green, 2.5% ammonium molybdate and 0.2% Tween 20).

(ii) Calcineurin

Calmodulin was prepared from bovine brain according to the method of Wallace et al. (Wallace, R. W., E. A. Tallant and W. Y. Chung [1983] "Assay of calmodulin by $Ca^{2+}$ dependent phosphodiesterase" *Meth. Enzymol.* 102:244–286). The calmodulin was either used directly or coupled to sepharose-4B to form the calmodulin-sepharose affinity column necessary for the isolation of calcineurin. Calcineurin was prepared from bovine brain by the method of Tallant et al. (Tallant, E. A., R. W. Wallace and W. Y. Chung [1983] "Purification and radioimmunoassay of calmodulin-dependent protein phosphatase from bovine brain" *Meth. Enzymol.* 102:244–286), concentrated, aliquoted and stored at −80° C.

Calcineurin activity was assayed in 96-well microtiter plates in a final volume of 50 μl. Each well contained 50 mM Tris-HCI pH 7.5, 0.5 mM $MnCl_2$, 0.05 mM $CaCl_2$, 1 mM DTT, 50 mM p-nitrophenylphosphate (pNPP), 0.3 μg calcineurin, a five-fold excess of calmodulin, and either test samples or control compounds. Plates were incubated at 30° C. for 60 min. Liberated p-nitrophenol was determined by the change in absorbance at 405 nm.

(iii) cdc25A cdc25A was prepared as a recombinant protein expressed in *Escherichia coli*. The phosphatase activity of the enzyme was assayed in a final volume of 200 μl in 96-well plates by the method of Baratte et al. (Baratte, B., L. Meijer, K. Galatnikov and D. Beach (1992) "Screening for antimitotic compounds using the cdc25 tyrosine phosphatase, an activator of the mitosis-inducing $p34^{cdc2}$/cyclin $B^{cdc13}$ protein kinase" *Anticancer Research* 12:873–880). Each well contained 50 mM Tris-HCl pH 8.0, 50 mM NaCl, 1 mM EDTA, 15 mM DTT, 50 mM pNPP up to 10 μg recombinant protein and either test samples or controls. Plates were incubated at 37° C. for 90 minutes and the liberated p-nitrophenol determined by the change in absorbance at 405 nm. The assay (U.S. Pat. No. 5,294,538 assigned to Mitotix, Inc., Cambridge, Mass.) is used by HBOI under license from Mitotix.

(iv) DPPIV

Recombinant human DPP IV was produced through transient expression of a human DPP IV plasmid construct transfected into COS-7 cells by electroporation. The peptidase activity of this enzyme was determined in phosphate buffered saline (PBS) in a final volume of 200 μl in 96-well plates. Each well contained 200 mM gly-pro-pNA as substrate, 10 μl of the recombinant DPP IV and test samples or controls. Liberated p-nitroaniline was determined by the change in absorbance at 405 nm following a 60 min incubation at 37° C.

(v) Aminopeptidase N (CD13)

Aminopeptidase N was assayed using an Enzyme-Linked Immunosorbant (ELISA) capture assay. Briefly, 96-well plates were coated with goat anti-mouse immunoglobulins (Sigma #M4169). Following an overnight incubation the plates were washed three times with PBS-0.1% Triton X-100. The secondary (capture) antibody was then added to the plate (100 μl/well, 3.7 μg/ml; antihuman MY7, Coulter Corporation) and incubated for 3 hours at room temperature. Plates were washed three times with PBS-0.1% Triton X-100. The source of Aminopeptidase N was the KG-1 cell line, 100 μl of an appropriate dilution of the KG-1 cell lysate was added to each well, incubated for 3 hours and then washed a final time. The enzyme assay was performed in PBS in a final volume of 200 μl with 200 μM ala-pNA as substrate and either test samples or controls. Liberated p-nitroaniline was determined by the change in absorbance at 405 nm following an 18 hr incubation at 37° C.

(vi) CPP32

Test samples were aliquoted into 96 well microtiter plates and allowed to air dry. The stock CPP32 enzyme (BASF, Worcester, Mass.) was diluted by adding 10 μl of the enzyme to 17 ml of reaction buffer (50 mM Hepes pH 7.5; 10% glyccrol; 5 mM Dithiothreitol; 0.5 mM EDTA). A volume of 180 μl of the diluted enzyme was added to wells containing the dried test samples, or to empty wells (control). The contents of the microtiter wells were mixed by shaking on a plate shaker. Plates were incubated at 30° C. for 5 minutes. A volume of 20 μl of substrate (Ac-DEVD-pNA) was added to each well which resulted in a final concentration of 25 μM. Controls for each plate consisted of an inhibitor control (50 nM DEVD-CHO final concentration); positive control (enzyme and substrate) and negative control (reaction buffer substrate). The plates were covered with aluminum foil and mixed using a plate shaker for 5 min. then incubated at 30° C. for 30 minutes. Plates were read using a plate reader with absorbance measured at 405 nm. Data was expressed as percent inhibition by comparing the absorbance values of test samples with those of the positive control (no sample). The $IC_{50}$ determination was defined as the concentration of sample/pure compound which resulted in a 50% inhibition of the enzyme-substrate absorbance value.

(vii) ICE

Test samples were aliquoted into 96 well microtiter plates and allowed to air dry. Stock ICE enzyme (supplied by BASF, Worcester, Mass.) was diluted in reaction buffer (50 mM Hepes pH 7.5, 10% glycerol, 5 mM dithiothreitol, 0.5 mM EDTA and 5 mM β-mercaptoethanol) to a concentration that yielded a minimum increase of 0.1 optical density units after 30 minutes of reaction time. Diluted ICE enzyme was incubated at room temperature for 5 minutes prior to aliquoting 180 μl into each sample well. The plates were incubated at 30° C. for 5 minutes following a brief mixing of the well contents by shaking on a plate shaker. A volume of 20 μl of the enzyme substrate (Ac-YVAD-pNA) was added to each well resulting in a final concentration of 50 μM. Controls for each plate consisted of an inhibitor control (50 nM YVAD-CHO final concentration); positive control (enzyme and substrate) and negative control (reaction buffer and substrate). The plates were covered with aluminum foil and mixed using a plate shaker for 15 seconds, then incubated at 30° C. for 30 minutes. Plates were read on a plate reader with absorbance measured at 405 nm. Data was expressed as percent inhibition by comparing the absorbance values of test samples with those of the positive control (no sample). The $IC_{50}$ determination was defined as the concentration of sample or pure compound which resulted in a 50% inhibition of the enzyme-substrate absorbance value.

Following are examples which illustrate procedures for practicing the invention. These examples should not be construed as limiting. All percentages are by weight and all solvent mixture proportions are by volume unless otherwise noted.

Example 1—Isolation and Biological Activity of Secobatzelline A and Secobatzelline B FIG. 2 shows a schematic for the isolation of the subject compounds from a marine sponge.

Example 2—Chemical and Physical Characterization of Secobatzelline A and Secobatzelline B Structure 1 (Secobatzelline A)

Dark orange colored non-crystalline compound, mp>300° C., $(\alpha)_D$—135° (c 0.01, $CH_3OH$)

Molecular Weight 255 (257 for Cl isotope)

Molecular Formula $C_{10}H_{11}ClN_3O_3$ (HRFABMS, NBA) m/z, 256.055, Δ6 mmu and 358.051, Δ5 mmu for M+H UV (MeOH) λmax 322 (ε 10,100), 233 (13,600), 203 (15,700) nm IR (KBr) ν max 3237, 2917, 1658, 1611, 1585, 1500, 1408, 1360, 1024, and 752 $cm^{-1}$ $^1H$ NMR (500 MHz, DMSO-$d_6$)δ 12.5 (1H, br s,NH-1), 9.80 (1H, br s, NH-10), 7.16 (1H, s, H-2), 6.55 (2H, br s, NH-11), 4.67 (1H, t, J=6.1 Hz, H-8), 3.49 (2H, d, J=6.1 Hz, H-9)

$^{13}C$ NMR (90.5 MHz, DMSO-$d_6$) δ 169.3 (s, C-7), 158.0 (s, C-4), 141.2 (s, C-6), 127.1 (s, C-7a), 127.1 (s, C-3), 125.8 (d, C-2), 124.4 (s, C-3a), 103.9 (s, C-5), 67.8 (d, C-8), 65.4 (t, C-9)

Structure 2 (Secobatzelline B)

Red non-crystalline compound, mp>300° C., $(\alpha)_D$—18° (c 0.01, $CH_3OH$)

Molecular Weight 256 (258 for Cl isotope)

Molecular Formula $C_{10}H_{10}ClN_2O_4$ (HRFABMS, magic bullet) weak m/z 257.043, 259.040 for M+H UV (MeOH) λ max 335 (ε 21,200), 245sh (10,200), 203 (21,200)nm IR (KBr) ν max 3456, 3347, 2918, 1667, 1623, 1580, 1549, 1509, 1408, 1351, 1290, 1060, 890, and 830 $cm^{-1}$ $^1H$ NMR (360 MHz, $CD_3COCD_3$ and 10% DMSO-$d_6$) δ7.18 (1H, s, H-2), 6.63 (1H, br s, NH), 4.90 (1H, dd, J=6.6, 4.7 Hz, H-8), 3.65 (1H, dd, J=10.8, 4.7 Hz, H-9), 3.50 (1H, dd, J=10.8, 6.6 Hz, H-9)

$^1H$ NMR (500 MHz, DMSO-$d_6$) δ 12.63 (1H, br s, H-1), 7.11 (1H, s, H-2), 7.09 (2H, br s, NH-11),5.10 (1H, d, J=5.5 Hz, OH-8),4.87 (1H, ddd, J=6, 5.5, 5.5 Hz, H-8),4.57 (1H, t, J=6.0 Hz, OH-9),3.49 (1H, ddd, J=9, 5.5, 6 Hz, H-9),3.27 (1H, ddd, J=9, 5.5, 6 Hz, H-9).

$^{13}C$ NMR (125.7 MHz, DMSO-$d_6$) δ 175.8 (s, C-4), 169.5 (s, C-7), 145.9 (s, C-6), 129.0 (s, C-3), 127.5 (s, C-7a), 126.3 (d, C-2), 122.5 (s, C-3a), 104.9 (s, C-5), 67.5 (d, C-8), 66.0 (t, C-9).

Example 3—Activity of crude extract of 25- VIII-94-1-001

|  | cdc25 % I | PYP3 % I | CaN % I | CaN, $IC_{50}$ μg/mL | LAR % I | CD45 % I | DPP-IV % I |
|---|---|---|---|---|---|---|---|
| $1^{st}$ EtOH ext. | 7 | −3 | 87 | Not tested | 91 | 0 | 14 |
| $2^{nd}$ EtOH ext. | 0 | −8 | 86 | Not tested | 92 | 07 | 24 |
| $H_2O$ partition | −6 | −14 | 86 | 7.9 | 32 | −23 | 7 |
| BuOH partition | −4 | −6 | 85 | 6.8 | 26 | −5 | 18 |

Concentration tested: 5 μg/mL except LAR 50 μg/mL

Example 4—Activity of crude extract of 26-VIII-94-4-003

|  | cdc25 % I | PYP3 % I | CaN % I | CaN, $IC_{50}$ μg/mL | LAR % I | CD45 % I | DPP-IV % I |
|---|---|---|---|---|---|---|---|
| $1^{st}$ EtOH ext. | 7 | −3 | 89 | Not tested | 94 | −4 | 12 |
| $2^{nd}$ EtOH ext. | −2 | −6 | 89 | Not tested | 96 | −24 | 13 |
| $H_2O$ partition | 0 | −6 | 88 | 5.8 | 28 | −8 | 14 |
| BuOH partition | 4 | 4 | 86 | 4.5 | 22 | −19 | 13 |

Concentration tested: 5 μg/mL except LAR 50 μg/mL

Example 5—Biological Activity of Secobatzelline A and Secobatzelline B

Biological activity data for these compounds are as follows;

Biological Activity data: Secobatzelline A (1)

CaN, I=75% at 5 μg/ml

CaN, I=46% at 0.5 μg/ml

CaN, $IC_{50}$=0.55 μg/ml

ApN, I=54.9% at 5 μg/ml

P388, $IC_{50}$=0.06 μg/ml

A549, $IC_{50}$=0.04 μg/ml

EL-4, inh. adhesion

MLR, $IC_{50}$=0.68 μg/ml

LCV, $IC_{50}$=1.4 μg/ml

ICE, not detected

CPP32, I=86.5% at 5 μg/ml

CPP32, I=76.2% at 0.5 μg/ml

CPP32, $IC_{50}$=0.02 μg/ml

Biological activity data: Secobatzelline B (2)

CaN, I=43% at 5 μg/ml

CaN, I=22% at 0.5 μg/ml

CaN, $IC_{50}$=2.21 μg/ml

P388, $IC_{50}$=1.22 μg/ml

A549, $IC_{50}$=2.86 μg/ml

Example 6—Acetylation of Secobatzelline A

Acetylation of 18SG541(secobatzelline-A): A solution of 18SG541 (10.0 mg) in pyridine (1.5 ml) and acetic anhydride (0.5 ml) was stirred at 50° C. for 4 hours. The solvent was removed in vacuum, and the resulting oil was purified by HPLC (SiO$_2$, 5 mm, 250×10 mm) with 2% MeOH/CH$_2$Cl$_2$ to give pure diacetates.

Example 7—Diacetate of Secobatzelline A

18SG791 (Structure 3) (same as 18SG541-diacetate)

Orange colored non-crystalline compound, mp 169°–70° C., $(\alpha)_D$—$^{24°}$ (c 0.01, CH$_3$OH)

Molecular Weight 339 (341 for Cl isotope)

Molecular Formula C$_{14}$H$_{14}$ClN$_3$O$_5$ (HRFABMS, NBA) m/z, 340.054, Δ2 mmu and 342.047, Δ5 mmu for M$^+$H.

UV (MeOH) λmax 320 (ε 12,900), 227 (21,100), 203 (23,200) nm

IR (Neat) λmax 3225, 2930, 1726, 1651, 1623, 1229, 1216, 1021, and 765 cm$^{-1}$ $^1$H NMR (500 MHz, DMSO-d$_6$) δ12.65 (1H, br s, NH-1), 10.15 (1H, br s, NH-10), 7.27 (1H, s, H-2), 6.55 (1H, t, J=6.7 Hz, H-8), 6.41 (2H, br s, NH-11), 4.30 (2H, dd, J=11.1, 6.7 Hz,), 2.06 (3H, s, OAc), 1.98 (3H, s OAc).

$^{13}$C NMR (125.7 MHz, CDCl$_3$/10%CD$_3$OD) δ171.1 (s, OAc), 170.2 (s, OAc), 169.9 (s, C-7), 157.4 (s, C-4), 139.5 (s,C-6), 127.3 (s, C-7a), 125.1, (d, C-2), 124.1 (s, C-3a), 120.8 (s, C-3), 107.3 (s, C-5), 68.2 (d, C-8), 64.9 (t, C-9), 20.8 (q, OAc), 20.6 (q, OAc).

$^{13}$C NMR (125.7 MHz, DMSO-d$_6$) δ169.8 (s, OAc), 169.5 (s, C-7), 169.4 (s, OAc), 157.2 (s, C-4), 140.2 (s, C-6), 127.0 (s, C-7a), 125.6 (d, C-2), 124.0 (s, C-3a), 120.1 (s, C-3), 104.1 (s, C-5), 67.5 (d, C-8), 64.9 (t, C-9), 20.6 (q, OAc), 20.3 (q, OAc).

Example 8—Diacetate of Secobatzelline B

18SG792 (Structure 4) (same as 18SG542-diacetate)

Dark pink non-crystalline compound, mp 170°–171° C.

Molecular Weight 340 (342 for Cl isotope)

Molecular Formula C$_{14}$H$_{13}$ClN$_2$O$_6$

UV (MeOH) λmax 342 (ε 5,400), 303 (14,300), 238 (18,700), 205 (19,500) nm

IR (Neat) ν max 3162, 2930, 1733, 1677, 1605, 1402, 1242, 1232, and 1042 cm$^{-1}$ $^1$H NMR (500 MHz, DMSO-d$_6$) δ12.80 (1H, br s, NH-1), 7.28 (1H, s, H-2), 7.13 (2H, br s, NH-11), 6.30 (1H, dd, J=6.3, 6.2 Hz, H-8), 4.27 (2H, m, H-9), 2.04 (3H, s, OAc), 1.98 (3H, s, OAc).

$^{13}$C NMR (125.7 MHz, DMSO-d$_6$) δ175.2 (s, C-4), 170.0 (2C, s, OAc), 169.6 (s, C-7), 145.9 (s, C-6), 128.0 (s, C-7a), 126.5 (s, C-2), 122.4 (d, C-3a), 121.4 (s, C-3) 105.1 (s, C-5), 66.8 (d, C-8), 64.3 (t, C-9), 20.8 (q, OAc), 20.6 (q, OAc).

Example 9—Formulation and Administration

The compounds of the invention are useful for various non-therapeutic and therapeutic purposes. It is apparent from the testing that the compounds of the invention are effective for anti-inflammatory, neuroprotective, anti-proliferative, and immunomodulatory uses.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

In a one embodiment, when used as anti-inflammatory agents, the compounds or compositions of the subject invention are administered in a lotion or other cosmetic preparation. This administration is done directly to the skin where anti-inflammatory activity is desired.

Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

In another embodiment, compounds of the subject invention have effective immunomodulatory activity. Specifically, they are useful in regulating immune responses in animals and humans. Thus, pharmaceutical compositions containing compounds of the invention as active ingredients are useful in prophylactic or therapeutic treatment of an immunomodulatory response in humans or other mammals.

In one embodiment, the compounds of the subject invention can be used for modulation of T cell activity. Thus, one aspect of the subject invention concerns human in vivo suppression of T cell response, e.g., transplantation and autoimmunity.

The dosage administration to a host in the above indications will be dependent upon the identity of the condition to be treated, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the invention compounds, as a first active ingredient plus a second active ingredient comprising, for example, an anti-inflammatory, anti-proliferative, or immunomodulatory compound known in the art. Known anti-inflammatory drugs include, but are not limited to, the steroidal anti-inflammatory drugs and the non-steroidal anti-inflammatory drugs (NSAIDs).

In accordance with this invention, pharmaceutically effective amounts of a previously-known biologically active agent and the aminoiminoquinone and/or aminoquinone compounds (or secobatzellines) of the subject invention are administered sequentially or concurrently to the patient. The most effective mode of administration and dosage regimen of the compounds of the subject invention will depend upon the type of condition to be treated, the severity and course of that condition, previous therapy, the patient's health status, and response to the compounds and the judgment of the treating physician. The compositions of the subject invention may be administered to the patient at one time or over a series of treatments.

Preferably, the compositions of the subject invention, and any second agent are administered sequentially to the patient, with the second agent being administered before, after, or both before and after treatment with the aminoiminoquinone and/or aminoquinone compound(s). Sequential administration involves treatment with the second agent at least on the same day (within 24 hours) of treatment with the compounds of the subject invention and may involve continued treatment with the second agent on days that the compound(s) of the subject invention is not administered. Conventional modes of administration and standard dosage regimens of active agents may be used (see Gilman, A. G. et al. [eds.] *The Pharmacological Basis of Therapeutics,* pp. 697–713, 1482, 1489–91 [1980]; *Physicians Desk Reference,* 1986 Edition). For example, indomethacin can be administered orally at a dosage of about 25–50 mg, three times a day. Higher doses can also be used. Alternatively, aspirin (about 1500–2000 mg/day), ibuprofen (about 1200–3200 mg/day), or conventional therapeutic doses of other agents can be used. Dosages of active agents can be titrated to the individual patient.

According to one embodiment of this invention, the patient may receive concurrent treatments with a second active ingredient and compositions comprising the compounds of the subject invention. For example, local, intralesional, or intravenous injection of the aminoiminoquinones and/or aminoquinones is preferred (see Gilman et al., supra at pp. 1290–91). The agents can be administered by subcutaneous injection, subcutaneous slow-release implant, or orally.

Alternatively, the patient can receive a composition comprising a combination of one or more compounds of the subject invention and a second active agent according to conventional modes of administration of agents which exhibit antibacterial, anticancer, immunomodulatory, antitumor, or anti-inflammatory activity. These include, for example, parenteral, subcutaneous, intravenous, or intralesional routes of administration.

The compositions used in these therapies can also be in a variety of forms. These include, for example, solid, semisolid, and liquid dosage forms, such as tablets, pills, powders, liquid solutions or suspension, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch, and equivalent carriers and diluents. While effective amounts may vary, as conditions in which compositions are used vary, a minimal dosage required for anti-inflammatory activity is generally between 0.01 and 100 µg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 50 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 50 mg/kg; and aerosol, 0.01 to about 50 mg/kg of animal (body) weight.

Once improvement of the patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A compound selected from the group consisting of Secobatzelline A and Secobatzelline B, and analogs, salts, and derivatives thereof.

2. The compound, according to claim 1, wherein said compound is Secobatzelline A.

3. The compound, according to claim 1, wherein said compound is Secobatzelline B.

4. A compound having the following structural formula:

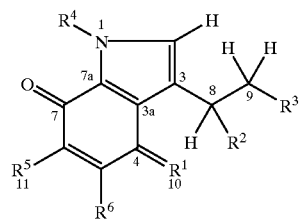

wherein $R^1$ is NH or O;

$R^2$ is OZ;

$R^3$ is OZ;

$R^4$ is H or R;

$R^5$ is $NH_2$, $NR_2$, or OZ; and $R^6$ is H or X;

wherein Z is selected from the group consisting of H, R, COR, mesyl, tosyl, glutamyl, succinyl, and malonyl;

R is selected from the group consisting of C1 to C8 alkyl, phenyl, and benzyl; and X is Cl, Br, or I.

5. The compound, according to claim 4, wherein $R^1$ is NH; $R^2$ is OH; $R^3$ is OH; $R^4$ is H; $R^5$ is $NH_2$ and $R^6$ is Cl.

6. The compound, according to claim 4, wherein $R^1$ is NH; $R^2$ is OCOR; $R^3$ is OCOR; $R^4$ is H; $R^5$ is $NH_2$; and $R^6$ is Cl.

7. The compound, according to claim 4, wherein $R^1$ is O; $R^2$ is OH; $R^3$ is OH; $R^4$ is H; $R^5$ is $NH_2$; and $R^6$ is Cl.

8. The compound, according to claim 4, wherein $R^1$ is O; $R^2$ is OCOR; $R^3$ is OCOR; $R^4$ is H; $R^5$ is $NH_2$; and $R^6$ is Cl.

9. The compound, according to claim 4, wherein said compound is selected from the group consisting of:

| | |
|---|---|
| Analog (5) | $R^1$ = NH, $R^2$ = OH, $R^3$ = OCOR, $R^4$ = H, $R^5$ = $NH_2$, $R^6$ = X |
| Analog (6) | $R^1$ = NH, $R^2$ = OH, $R^3$ = OZ, $R^4$ = H, $R^5$ = $NH_2$, $R^6$ = X |
| Analog (7) | $R^1$ = NH, $R^2$ = OCOR, $R^3$ = OH, $R^4$ = H, $R^5$ = $NH_2$, $R^6$ = X |
| Analog (8) | $R^1$ = NH, $R^2$ = OZ, $R^3$ = OH, $R^4$ = H, $R^5$ = $NH_2$, $R^6$ = X |
| Analog (9) | $R^1$ = O, $R^2$ = OH, $R^3$ = OCOR, $R^4$ = H, $R^5$ = $NH_2$, $R^6$ = X |
| Analog (10) | $R^1$ = O, $R^2$ = OH, $R^3$ = OZ, $R^4$ = H, $R^5$ = $NH_2$, $R^6$ = X |
| Analog (11) | $R^1$ = O, $R^2$ = OCOR, $R^3$ = OH, $R^4$ = H, $R^5$ = $NH_2$, $R^6$ = X |
| Analog (12) | $R^1$ = O, $R^2$ = OZ, $R^3$ = OH, $R^4$ = H, $R^5$ = $NH_2$, $R^6$ = X |
| Analog (13) | $R^1$ = NH, $R^2$ = OH, $R^3$ = OH, $R^4$ = R, $R^5$ = $NH_2$, $R^6$ = X |
| Analog (14) | $R^1$ = O, $R^2$ = OH, $R^3$ = OH, $R^4$ = R, $R^5$ = $NH_2$, $R^6$ = X |
| Analog (15) | $R^1$ = NH, $R^2$ = OH, $R^3$ = OH, $R^4$ = H, $R^5$ = $NR_2$, $R^6$ = X |
| Analog (16) | $R^1$ = O, $R^2$ = OH, $R^3$ = OH, $R^4$ = H, $R^5$ = $NR_2$, $R^6$ = X |
| Analog (17) | $R^1$ = NH, $R^2$ = OH, $R^3$ = OH, $R^4$ = R, $R^5$ = $NR_2$, $R^6$ = X |
| Analog (18) | $R^1$ = O, $R^2$ = OH, $R^3$ = OH, $R^4$ = R, $R^5$ = $NR_2$, $R^6$ = X |
| Analog (19) | $R^1$ = NH, $R^2$ = OCOR, $R^3$ = OCOR, $R^4$ = R, $R^5$ = $NH_2$, $R^6$ = X |
| Analog (20) | $R^1$ = NH, $R^2$ = OZ, $R^3$ = OZ, $R^4$ = R, $R^5$ = $NH_2$, $R^6$ = X |
| Analog (21) | $R^1$ = O, $R^2$ = OCOR, $R^3$ = OCOR, $R^4$ = R, $R^5$ = $NH_2$, $R^6$ = X |
| Analog (22) | $R^1$ = O, $R^2$ = OZ, $R^3$ = OZ, $R^4$ = R, $R^5$ = $NH_2$, $R^6$ = X |
| Analog (23) | $R^1$ = NH, $R^2$ = OCOR, $R^3$ = OH, $R^4$ = H, $R^5$ = $NR_2$, $R^6$ = X |
| Analog (24) | $R^1$ = NH, $R^2$ = OZ, $R^3$ = OH, $R^4$ = H, $R^5$ = $NR_2$, $R^6$ = X |
| Analog (25) | $R^1$ = O, $R^2$ = OCOR, $R^3$ = OH, $R^4$ = H, $R^5$ = $NR_2$, $R^6$ = X |
| Analog (26) | $R^1$ = O, $R^2$ = OZ, $R^3$ = OH, $R^4$ = H, $R^5$ = $NR_2$, $R^6$ = X |
| Analog (27) | $R^1$ = NH, $R^2$ = OH, $R^3$ = OCOR, $R^4$ = R, $R^5$ = $NR_2$, $R^6$ = X |
| Analog (28) | $R^1$ = NH, $R^2$ = OH, $R^3$ = OZ, $R^4$ = R, $R^5$ = $NR_2$, $R^6$ = X |
| Analog (29) | $R^1$ = O, $R^2$ = OH, $R^3$ = OCOR, $R^4$ = R, $R^5$ = $NR_2$, $R^6$ = X |
| Analog (30) | $R^1$ = O, $R^2$ = OH, $R^3$ = OZ, $R^4$ = R, $R^5$ = $NR_2$, $R^6$ = X |
| Analog (31) | $R^1$ = NH, $R^2$ = OCOR, $R^3$ = OCOR, $R^4$ = H, $R^5$ = $NH_2$, $R^6$ = H |
| Analog (32) | $R^1$ = NH, $R^2$ = OZ, $R^3$ = OZ, $R^4$ = H, $R^5$ = $NH_2$, $R^6$ = H |
| Analog (33) | $R^1$ = O, $R^2$ = OCOR, $R^3$ = OCOR, $R^4$ = H, $R^5$ = $NH_2$, $R^6$ = H |
| Analog (34) | $R^1$ = O, $R^2$ = OZ, $R^3$ = OZ, $R^4$ = H, $R^5$ = $NH_2$, $R^6$ = H |
| Analog (35) | $R^1$ = NH, $R^2$ = OH, $R^3$ = OCOR, $R^4$ = H, $R^5$ = $NH_2$, $R^6$ = H |
| Analog (36) | $R^1$ = NH, $R^2$ = OH, $R^3$ = OZ, $R^4$ = H, $R^5$ = $NH_2$, $R^6$ = H |
| Analog (37) | $R^1$ = NH, $R^2$ = OCOR, $R^3$ = OH, $R^4$ = H, $R^5$ = $NH_2$, $R^6$ = H |
| Analog (38) | $R^1$ = NH, $R^2$ = OZ, $R^3$ = OH, $R^4$ = H, $R^5$ = $NH_2$, $R^6$ = H |
| Analog (39) | $R^1$ = O, $R^2$ = OH, $R^3$ = OCOR, $R^4$ = H, $R^5$ = $NH_2$, $R^6$ = H |
| Analog (40) | $R^1$ = O, $R^2$ = OH, $R^3$ = OZ, $R^4$ = H, $R^5$ = $NH_2$, $R^6$ = H |
| Analog (41) | $R^1$ = O, $R^2$ = OCOR, $R^3$ = OH, $R^4$ = H, $R^5$ = $NH_2$, $R^6$ = H |
| Analog (42) | $R^1$ = O, $R^2$ = OZ, $R^3$ = OH, $R^4$ = H, $R^5$ = $NH_2$, $R^6$ = H |
| Analog (43) | $R^1$ = NH, $R^2$ = OH, $R^3$ = OH, $R^4$ = R, $R^5$ = $NH_2$, $R^6$ = H |
| Analog (44) | $R^1$ = O, $R^2$ = OH, $R^3$ = OH, $R^4$ = R, $R^5$ = $NH_2$, $R^6$ = H |
| Analog (45) | $R^1$ = NH, $R^2$ = OH, $R^3$ = OH, $R^4$ = H, $R^5$ = $NR_2$, $R^6$ = H |
| Analog (46) | $R^1$ = O, $R^2$ = OH, $R^3$ = OH, $R^4$ = H, $R^5$ = $NR_2$, $R^6$ = H |
| Analog (47) | $R^1$ = NH, $R^2$ = OH, $R^3$ = OH, $R^4$ = R, $R^5$ = $NR_2$, $R^6$ = H |
| Analog (48) | $R^1$ = O, $R^2$ = OH, $R^3$ = OH, $R^4$ = R, $R^5$ = $NR_2$, $R^6$ = H |
| Analog (49) | $R^1$ = NH, $R^2$ = OCOR, $R^3$ = OCOR, $R^4$ = R, $R^5$ = $NH_2$, $R^6$ = H |
| Analog (50) | $R^1$ = NH, $R^2$ = OZ, $R^3$ = OZ, $R^4$ = R, $R^5$ = $NH_2$, $R^6$ = H |
| Analog (51) | $R^1$ = O, $R^2$ = OCOR, $R^3$ = OCOR, $R^4$ = R, $R^5$ = $NH_2$, $R^6$ = H |
| Analog (52) | $R^1$ = O, $R^2$ = OZ, $R^3$ = OZ, $R^4$ = R, $R^5$ = $NH_2$, $R^6$ = H |
| Analog (53) | $R^1$ = NH, $R^2$ = OCOR, $R^3$ = OH, $R^4$ = H, $R^5$ = $NR_2$, $R^6$ = H |
| Analog (54) | $R^1$ = NH, $R^2$ = OZ, $R^3$ = OH, $R^4$ = H, $R^5$ = $NR_2$, $R^6$ = H |
| Analog (55) | $R^1$ = O, $R^2$ = OCOR, $R^3$ = OH, $R^4$ = H, $R^5$ = $NR_2$, $R^6$ = H |
| Analog (56) | $R^1$ = O, $R^2$ = OZ, $R^3$ = OH, $R^4$ = H, $R^5$ = $NR_2$, $R^6$ = H |
| Analog (57) | $R^1$ = NH, $R^2$ = OH, $R^3$ = OCOR, $R^4$ = R, $R^5$ = $NR_2$, $R^6$ = H |
| Analog (58) | $R^1$ = NH, $R^2$ = OH, $R^3$ = OZ, $R^4$ = R, $R^5$ = $NR_2$, $R^6$ = H |
| Analog (59) | $R^1$ = O, $R^2$ = OH, $R^3$ = OCOR, $R^4$ = R, $R^5$ = $NR_2$, $R^6$ = H |
| Analog (60) | $R^1$ = O, $R^2$ = OH, $R^3$ = OZ, $R^4$ = R, $R^5$ = $NR_2$, $R^6$ = H |
| Analog (61) | $R^1$ = NH, $R^2$ = OCOR, $R^3$ = OCOR, $R^4$ = H, $R^5$ = OH, $R^6$ = X |
| Analog (62) | $R^1$ = NH, $R^2$ = OZ, $R^3$ = OZ, $R^4$ = H, $R^5$ = OH, $R^6$ = X |
| Analog (63) | $R^1$ = NH, $R^2$ = OCOR, $R^3$ = OCOR, $R^4$ = H, $R^5$ = OCOR, $R^6$ = X |
| Analog (64) | $R^1$ = NH, $R^2$ = OZ, $R^3$ = OZ, $R^4$ = H, $R^5$ = OZ, $R^6$ = X |
| Analog (65) | $R^1$ = O, $R^2$ = OCOR, $R^3$ = OCOR, $R^4$ = H, $R^5$ = OH, $R^6$ = X |
| Analog (66) | $R^1$ = O, $R^2$ = OZ, $R^3$ = OZ, $R^4$ = H, $R^5$ = OH, $R^6$ = X |
| Analog (67) | $R^1$ = O, $R^2$ = OCOR, $R^3$ = OCOR, $R^4$ = H, $R^5$ = OCOR, $R^6$ = X |
| Analog (68) | $R^1$ = O, $R^2$ = OZ, $R^3$ = OZ, $R^4$ = H, $R^5$ = OZ, $R^6$ = X |
| Analog (69) | $R^1$ = NH, $R^2$ = OH, $R^3$ = OH, $R^4$ = H, $R^5$ = OH, $R^6$ = X |
| Analog (70) | $R^1$ = O, $R^2$ = OH, $R^3$ = OH, $R^4$ = H, $R^5$ = OH, $R^6$ = X |
| Analog (71) | $R^1$ = NH, $R^2$ = OH, $R^3$ = OH, $R^4$ = R, $R^5$ = OH, $R^6$ = X |
| Analog (72) | $R^1$ = O, $R^2$ = OH, $R^3$ = OH, $R^4$ = R, $R^5$ = OH, $R^6$ = X |
| Analog (73) | $R^1$ = NH, $R^2$ = OCOR, $R^3$ = OCOR, $R^4$ = R, $R^5$ = OH, $R^6$ = X |
| Analog (74) | $R^1$ = NH, $R^2$ = OZ, $R^3$ = OZ, $R^4$ = R, $R^5$ = OH, $R^6$ = X |
| Analog (75) | $R^1$ = NH, $R^2$ = OCOR, $R^3$ = OCOR, $R^4$ = R, $R^5$ = OCOR, $R^6$ = X |
| Analog (76) | $R^1$ = NH, $R^2$ = OZ, $R^3$ = OZ, $R^4$ = R, $R^5$ = OZ, $R^6$ = X |
| Analog (77) | $R^1$ = O, $R^2$ = OCOR, $R^3$ = OCOR, $R^4$ = R, $R^5$ = $OH_2$, $R^6$ = X |
| Analog (78) | $R^1$ = O, $R^2$ = OZ, $R^3$ = OZ, $R^4$ = R, $R^5$ = $OH_2$, $R^6$ = X |
| Analog (79) | $R^1$ = O, $R^2$ = OCOR, $R^3$ = OCOR, $R^4$ = R, $R^5$ = OCOR, $R^6$ = X |
| Analog (80) | $R^1$ = O, $R^2$ = OZ, $R^3$ = OZ, $R^4$ = R, $R^5$ = OZ, $R^6$ = X |
| Analog (81) | $R^1$ = NH, $R^2$ = OCOR, $R^3$ = OH, $R^4$ = H, $R^5$ = OH, $R^6$ = X |
| Analog (82) | $R^1$ = NH, $R^2$ = OZ, $R^3$ = OH, $R^4$ = H, $R^5$ = OH, $R^6$ = X |
| Analog (83) | $R^1$ = O, $R^2$ = OCOR, $R^3$ = OH, $R^4$ = H, $R^5$ = OH, $R^6$ = X |

-continued

| | |
|---|---|
| Analog (84) | $R^1 = O, R^2 = OZ, R^3 = OH, R^4 = H, R^5 = OH, R^6 = X$ |
| Analog (85) | $R^1 = NH, R^2 = OH, R^3 = OCOR, R^4 = R, R^5 = OH, R^6 = X$ |
| Analog (86) | $R^1 = NH, R^2 = OH, R^3 = OZ, R^4 = R, R^5 = OH, R^6 = X$ |
| Analog (87) | $R^1 = O, R^2 = OH, R^3 = OCOR, R^4 = R, R^5 = OH, R^6 = X$ |
| Analog (88) | $R^1 = O, R^2 = OH, R^3 = OZ, R^4 = R, R^5 = OH, R^6 = X$ |
| Analog (89) | $R^1 = NH, R^2 = OCOR, R^3 = OCOR, R^4 = H, R^5 = OH, R^6 = H$ |
| Analog (90) | $R^1 = NH, R^2 = OZ, R^3 = OZ, R^4 = H, R^5 = OH, R^6 = H$ |
| Analog (91) | $R^1 = NH, R^2 = OCOR, R^3 = OCOR, R^4 = H, R^5 = OCOR, R^6 = H$ |
| Analog (92) | $R^1 = NH, R^2 = OZ, R^3 = OZ, R^4 = H, R^5 = OZ, R^6 = H$ |
| Analog (93) | $R^1 = O, R^2 = OCOR, R^3 = OCOR, R^4 = H, R^5 = OH, R^6 = H$ |
| Analog (94) | $R^1 = O, R^2 = OZ, R^3 = OZ, R^4 = H, R^5 = OH, R^6 = H$ |
| Analog (95) | $R^1 = O, R^2 = OCOR, R^3 = OCOR, R^4 = H, R^5 = OCOR, R^6 = H$ |
| Analog (96) | $R^1 = O, R^2 = OZ, R^3 = OZ, R^4 = H, R^5 = OZ, R^6 = H$ |
| Analog (97) | $R^1 = NH, R^2 = OH, R^3 = OH, R^4 = H, R^5 = OH, R^6 = H$ |
| Analog (98) | $R^1 = O, R^2 = OH, R^3 = OH, R^4 = H, R^5 = OH, R^6 = H$ |
| Analog (99) | $R^1 = NH, R^2 = OH, R^3 = OH, R^4 = R, R^5 = OH, R^6 = H$ |
| Analog (100) | $R^1 = O, R^2 = OH, R^3 = OH, R^4 = R, R^5 = OH, R^6 = H$ |
| Analog (101) | $R^1 = NH, R^2 = OCOR, R^3 = OCOR, R^4 = R, R^5 = OH, R^6 = H$ |
| Analog (102) | $R^1 = NH, R^2 = OZ, R^3 = OZ, R^4 = R, R^5 = OH, R^6 = H$ |
| Analog (103) | $R^1 = NH, R^2 = OCOR, R^3 = OCOR, R^4 = R, R^5 = OCOR, R^6 = H$ |
| Analog (104) | $R^1 = NH, R^2 = OZ, R^3 = OZ, R^4 = R, R^5 = OZ, R^6 = H$ |
| Analog (105) | $R^1 = O, R^2 = OCOR, R^3 = OCOR, R^4 = R, R^5 = OH_2, R^6 = H$ |
| Analog (106) | $R^1 = O, R^2 = OZ, R^3 = OZ, R^4 = R, R^5 = OH_2, R^6 = H$ |
| Analog (107) | $R^1 = O, R^2 = OCOR, R^3 = OCOR, R^4 = R, R^5 = OCOR, R^6 = H$ |
| Analog (108) | $R^1 = O, R^2 = OZ, R^3 = OZ, R^4 = R, R^5 = OZ, R^6 = H$ |
| Analog (109) | $R^1 = NH, R^2 = OCOR, R^3 = OH, R^4 = H, R^5 = OH, R^6 = H$ |
| Analog (110) | $R^1 = NH, R^2 = OZ, R^3 = OH, R^4 = H, R^5 = OH, R^6 = H$ |
| Analog (111) | $R^1 = O, R^2 = OCOR, R^3 = OH, R^4 = H, R^5 = OH, R^6 = H$ |
| Analog (112) | $R^1 = O, R^2 = OZ, R^3 = OH, R^4 = H, R^5 = OH, R^6 = H$ |
| Analog (113) | $R^1 = NH, R^2 = OH, R^3 = OCOR, R^4 = R, R^5 = OH, R^6 = H$ |
| Analog (114) | $R^1 = NH, R^2 = OH, R^3 = OZ, R^4 = R, R^5 = OH, R^6 = H$ |
| Analog (115) | $R^1 = O, R^2 = OH, R^3 = OCOR, R^4 = R, R^5 = OH, R^6 = H$ |
| Analog (116) | $R^1 = O, R^2 = OH, R^3 = OZ, R^4 = R, R^5 = OH, R^6 = H.$ |

10. A method for inhibiting inflammation in an animal wherein said method comprises administering to said animal an inflammation inhibiting amount of a compound having the following structure:

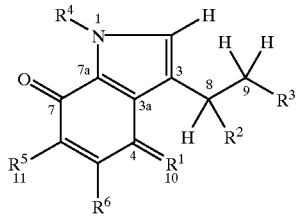

wherein $R^1$ is NH or O;
$R^2$ is OZ;
$R^3$ is OZ;
$R^4$ is H or R;

$R^5$ is $NH_2$, $NR_2$, or OZ; and
$R^6$ is H or X;

wherein Z is selected from the group consisting of H, R, COR, mesyl, tosyl, glutamyl, succinyl, and malonyl;

R is selected from the group consisting of C1 to C8 alkyl, phenyl, and benzyl; and X is Cl, Br, or I.

11. The method, according to claim 10, wherein $R^1$ is NH; $R^2$ is OH; $R^3$ is OH; $R^4$ is H; $R^5$ is $NH_2$ and $R^6$ is Cl.

12. The method, according to claim 10, wherein $R^1$ is NH; $R^2$ is OCOR; $R^3$ is OCOR; $R^4$ is H; $R^5$ is $NH_2$; and $R^6$ is Cl.

13. The method, according to claim 10, wherein $R^1$ is O; $R^2$ is OH; $R^3$ is OH; $R^4$ is H; $R^5$ is $NH_2$; and $R^6$ is Cl.

14. The method, according to claim 10, wherein $R^1$ is O; $R^2$ is OCOR; $R^3$ is OCOR; $R^4$ is H; $R^5$ is $NH_2$; and $R^6$ is Cl.

15. The method, according to claim 10, wherein said compound is selected from the group consisting of:

| | |
|---|---|
| Analog (5) | $R^1 = NH, R^2 = OH, R^3 = OCOR, R^4 = H, R^5 = NH_2, R^6 = X$ |
| Analog (6) | $R^1 = NH, R^2 = OH, R^3 = OZ, R^4 = H, R^5 = NH_2, R^6 = X$ |
| Analog (7) | $R^1 = NH, R^2 = OCOR, R^3 = OH, R^4 = H, R^5 = NH_2, R^6 = X$ |
| Analog (8) | $R^1 = NH, R^2 = OZ, R^3 = OH, R^4 = H, R^5 = NH_2, R^6 = X$ |
| Analog (9) | $R^1 = O, R^2 = OH, R^3 = OCOR, R^4 = H, R^5 = NH_2, R^6 = X$ |
| Analog (10) | $R^1 = O, R^2 = OH, R^3 = OZ, R^4 = H, R^5 = NH_2, R^6 = X$ |
| Analog (11) | $R^1 = O, R^2 = OCOR, R^3 = OH, R^4 = H, R^5 = NH_2, R^6 = X$ |
| Analog (12) | $R^1 = O, R^2 = OZ, R^3 = OH, R^4 = H, R^5 = NH_2, R^6 = X$ |
| Analog (13) | $R^1 = NH, R^2 = OH, R^3 = OH, R^4 = R, R^5 = NH_2, R^6 = X$ |
| Analog (14) | $R^1 = O, R^2 = OH, R^3 = OH, R^4 = R, R^5 = NH_2, R^6 = X$ |
| Analog (15) | $R^1 = NH, R^2 = OH, R^3 = OH, R^4 = H, R^5 = NR_2, R^6 = X$ |
| Analog (16) | $R^1 = O, R^2 = OH, R^3 = OH, R^4 = H, R^5 = NR_2, R^6 = X$ |
| Analog (17) | $R^1 = NH, R^2 = OH, R^3 = OH, R^4 = R, R^5 = NR_2, R^6 = X$ |
| Analog (18) | $R^1 = O, R^2 = OH, R^3 = OH, R^4 = R, R^5 = NR_2, R^6 = X$ |
| Analog (19) | $R^1 = NH, R^2 = OCOR, R^3 = OCOR, R^4 = R, R^5 = NH_2, R^6 = X$ |

-continued

| | |
|---|---|
| Analog (20) | $R^1$ = NH, $R^2$ = OZ, $R^3$ = OZ, $R^4$ = R, $R^5$ = $NH_2$, $R^6$ = X |
| Analog (21) | $R^1$ = O, $R^2$ = OCOR, $R^3$ = OCOR, $R^4$ = R, $R^5$ = $NH_2$, $R^6$ = X |
| Analog (22) | $R^1$ = O, $R^2$ = OZ, $R^3$ = OZ, $R^4$ = R, $R^5$ = $NH_2$, $R^6$ = X |
| Analog (23) | $R^1$ = NH, $R^2$ = OCOR, $R^3$ = OH, $R^4$ = H, $R^5$ = $NR_2$, $R^6$ = X |
| Analog (24) | $R^1$ = NH, $R^2$ = OZ, $R^3$ = OH, $R^4$ = H, $R^5$ = $NR_2$, $R^6$ = X |
| Analog (25) | $R^1$ = O, $R^2$ = OCOR, $R^3$ = OH, $R^4$ = H, $R^5$ = $NR_2$, $R^6$ = X |
| Analog (26) | $R^1$ = O, $R^2$ = OZ, $R^3$ = OH, $R^4$ = H, $R^5$ = $NR_2$, $R^6$ = X |
| Analog (27) | $R^1$ = NH, $R^2$ = OH, $R^3$ = OCOR, $R^4$ = R, $R^5$ = $NR_2$, $R^6$ = X |
| Analog (28) | $R^1$ = NH, $R^2$ = OH, $R^3$ = OZ, $R^4$ = R, $R^5$ = $NR_2$, $R^6$ = X |
| Analog (29) | $R^1$ = O, $R^2$ = OH, $R^3$ = OCOR, $R^4$ = R, $R^5$ = $NR_2$, $R^6$ = X |
| Analog (30) | $R^1$ = O, $R^2$ = OH, $R^3$ = OZ, $R^4$ = R, $R^5$ = $NR_2$, $R^6$ = X |
| Analog (31) | $R^1$ = NH, $R^2$ = OCOR, $R^3$ = OCOR, $R^4$ = H, $R^5$ = $NH_2$, $R^6$ = H |
| Analog (32) | $R^1$ = NH, $R^2$ = OZ, $R^3$ = OZ, $R^4$ = H, $R^5$ = $NH_2$, $R^6$ = H |
| Analog (33) | $R^1$ = O, $R^2$ = OCOR, $R^3$ = OCOR, $R^4$ = H, $R^5$ = $NH_2$, $R^6$ = H |
| Analog (34) | $R^1$ = O, $R^2$ = OZ, $R^3$ = OZ, $R^4$ = H, $R^5$ = $NH_2$, $R^6$ = H |
| Analog (35) | $R^1$ = NH, $R^2$ = OH, $R^3$ = OCOR, $R^4$ = H, $R^5$ = $NH_2$, $R^6$ = H |
| Analog (36) | $R^1$ = NH, $R^2$ = OH, $R^3$ = OZ, $R^4$ = H, $R^5$ = $NH_2$, $R^6$ = H |
| Analog (37) | $R^1$ = NH, $R^2$ = OCOR, $R^3$ = OH, $R^4$ = H, $R^5$ = $NH_2$, $R^6$ = H |
| Analog (38) | $R^1$ = NH, $R^2$ = OZ, $R^3$ = OH, $R^4$ = H, $R^5$ = $NH_2$, $R^6$ = H |
| Analog (39) | $R^1$ = O, $R^2$ = OH, $R^3$ = OCOR, $R^4$ = H, $R^5$ = $NH_2$, $R^6$ = H |
| Analog (40) | $R^1$ = O, $R^2$ = OH, $R^3$ = OZ, $R^4$ = H, $R^5$ = $NH_2$, $R^6$ = H |
| Analog (41) | $R^1$ = O, $R^2$ = OCOR, $R^3$ = OH, $R^4$ = H, $R^5$ = $NH_2$, $R^6$ = H |
| Analog (42) | $R^1$ = O, $R^2$ = OZ, $R^3$ = OH, $R^4$ = H, $R^5$ = $NH_2$, $R^6$ = H |
| Analog (43) | $R^1$ = NH, $R^2$ = OH, $R^3$ = OH, $R^4$ = R, $R^5$ = $NH_2$, $R^6$ = H |
| Analog (44) | $R^1$ = O, $R^2$ = OH, $R^3$ = OH, $R^4$ = R, $R^5$ = $NH_2$, $R^6$ = H |
| Analog (45) | $R^1$ = NH, $R^2$ = OH, $R^3$ = OH, $R^4$ = H, $R^5$ = $NR_2$, $R^6$ = H |
| Analog (46) | $R^1$ = O, $R^2$ = OH, $R^3$ = OH, $R^4$ = H, $R^5$ = $NR_2$, $R^6$ = H |
| Analog (47) | $R^1$ = NH, $R^2$ = OH, $R^3$ = OH, $R^4$ = R, $R^5$ = $NR_2$, $R^6$ = H |
| Analog (48) | $R^1$ = O, $R^2$ = OH, $R^3$ = OH, $R^4$ = R, $R^5$ = $NR_2$, $R^6$ = H |
| Analog (49) | $R^1$ = NH, $R^2$ = OCOR, $R^3$ = OCOR, $R^4$ = R, $R^5$ = $NH_2$, $R^6$ = H |
| Analog (50) | $R^1$ = NH, $R^2$ = OZ, $R^3$ = OZ, $R^4$ = R, $R^5$ = $NH_2$, $R^6$ = H |
| Analog (51) | $R^1$ = O, $R^2$ = OCOR, $R^3$ = OCOR, $R^4$ = R, $R^5$ = $NH_2$, $R^6$ = H |
| Analog (52) | $R^1$ = O, $R^2$ = OZ, $R^3$ = OZ, $R^4$ = R, $R^5$ = $NH_2$, $R^6$ = H |
| Analog (53) | $R^1$ = NH, $R^2$ = OCOR, $R^3$ = OH, $R^4$ = H, $R^5$ = $NR_2$, $R^6$ = H |
| Analog (54) | $R^1$ = NH, $R^2$ = OZ, $R^3$ = OH, $R^4$ = H, $R^5$ = $NR_2$, $R^6$ = H |
| Analog (55) | $R^1$ = O, $R^2$ = OCOR, $R^3$ = OH, $R^4$ = H, $R^5$ = $NR_2$, $R^6$ = H |
| Analog (56) | $R^1$ = O, $R^2$ = OZ, $R^3$ = OH, $R^4$ = H, $R^5$ = $NR_2$, $R^6$ = H |
| Analog (57) | $R^1$ = NH, $R^2$ = OH, $R^3$ = OCOR, $R^4$ = R, $R^5$ = $NR_2$, $R^6$ = H |
| Analog (58) | $R^1$ = NH, $R^2$ = OH, $R^3$ = OZ, $R^4$ = R, $R^5$ = $NR_2$, $R^6$ = H |
| Analog (59) | $R^1$ = O, $R^2$ = OH, $R^3$ = OCOR, $R^4$ = R, $R^5$ = $NR_2$, $R^6$ = H |
| Analog (60) | $R^1$ = O, $R^2$ = OH, $R^3$ = OZ, $R^4$ = R, $R^5$ = $NR_2$, $R^6$ = H |
| Analog (61) | $R^1$ = NH, $R^2$ = OCOR, $R^3$ = OCOR, $R^4$ = H, $R^5$ = OH, $R^6$ = X |
| Analog (62) | $R^1$ = NH, $R^2$ = OZ, $R^3$ = OZ, $R^4$ = H, $R^5$ = OH, $R^6$ = X |
| Analog (63) | $R^1$ = NH, $R^2$ = OCOR, $R^3$ = OCOR, $R^4$ = H, $R^5$ = OCOR, $R^6$ = X |
| Analog (64) | $R^1$ = NH, $R^2$ = OZ, $R^3$ = OZ, $R^4$ = H, $R^5$ = OZ, $R^6$ = X |
| Analog (65) | $R^1$ = O, $R^2$ = OCOR, $R^3$ = OCOR, $R^4$ = H, $R^5$ = OH, $R^6$ = X |
| Analog (66) | $R^1$ = O, $R^2$ = OZ, $R^3$ = OZ, $R^4$ = H, $R^5$ = OH, $R^6$ = X |
| Analog (67) | $R^1$ = O, $R^2$ = OCOR, $R^3$ = OCOR, $R^4$ = H, $R^5$ = OCOR, $R^6$ = X |
| Analog (68) | $R^1$ = O, $R^2$ = OZ, $R^3$ = OZ, $R^4$ = H, $R^5$ = OZ, $R^6$ = X |
| Analog (69) | $R^1$ = NH, $R^2$ = OH, $R^3$ = OH, $R^4$ = H, $R^5$ = OH, $R^6$ = X |
| Analog (70) | $R^1$ = O, $R^2$ = OH, $R^3$ = OH, $R^4$ = H, $R^5$ = OH, $R^6$ = X |
| Analog (71) | $R^1$ = NH, $R^2$ = OH, $R^3$ = OH, $R^4$ = R, $R^5$ = OH, $R^6$ = X |
| Analog (72) | $R^1$ = O, $R^2$ = OH, $R^3$ = OH, $R^4$ = R, $R^5$ = OH, $R^6$ = X |
| Analog (73) | $R^1$ = NH, $R^2$ = OCOR, $R^3$ = OCOR, $R^4$ = R, $R^5$ = OH, $R^6$ = X |
| Analog (74) | $R^1$ = NH, $R^2$ = OZ, $R^3$ = OZ, $R^4$ = R, $R^5$ = OH, $R^6$ = X |
| Analog (75) | $R^1$ = NH, $R^2$ = OCOR, $R^3$ = OCOR, $R^4$ = R, $R^5$ = OCOR, $R^6$ = X |
| Analog (76) | $R^1$ = NH, $R^2$ = OZ, $R^3$ = OZ, $R^4$ = R, $R^5$ = OZ, $R^6$ = X |
| Analog (77) | $R^1$ = O, $R^2$ = OCOR, $R^3$ = OCOR, $R^4$ = R, $R^5$ = $OH_2$, $R^6$ = X |
| Analog (78) | $R^1$ = O, $R^2$ = OZ, $R^3$ = OZ, $R^4$ = R, $R^5$ = $OH_2$, $R^6$ = X |
| Analog (79) | $R^1$ = O, $R^2$ = OCOR, $R^3$ = OCOR, $R^4$ = R, $R^5$ = OCOR, $R^6$ = X |
| Analog (80) | $R^1$ = O, $R^2$ = OZ, $R^3$ = OZ, $R^4$ = R, $R^5$ = OZ, $R^6$ = X |
| Analog (81) | $R^1$ = NH, $R^2$ = OCOR, $R^3$ = OH, $R^4$ = H, $R^5$ = OH, $R^6$ = X |
| Analog (82) | $R^1$ = NH, $R^2$ = OZ, $R^3$ = OH, $R^4$ = H, $R^5$ = OH, $R^6$ = X |
| Analog (83) | $R^1$ = O, $R^2$ = OCOR, $R^3$ = OH, $R^4$ = H, $R^5$ = OH, $R^6$ = X |
| Analog (84) | $R^1$ = O, $R^2$ = OZ, $R^3$ = OH, $R^4$ = H, $R^5$ = OH, $R^6$ = X |
| Analog (85) | $R^1$ = NH, $R^2$ = OH, $R^3$ = OCOR, $R^4$ = R, $R^5$ = OH, $R^6$ = X |
| Analog (86) | $R^1$ = NH, $R^2$ = OH, $R^3$ = OZ, $R^4$ = R, $R^5$ = OH, $R^6$ = X |
| Analog (87) | $R^1$ = O, $R^2$ = OH, $R^3$ = OCOR, $R^4$ = R, $R^5$ = OH, $R^6$ = X |
| Analog (88) | $R^1$ = O, $R^2$ = OH, $R^3$ = OZ, $R^4$ = R, $R^5$ = OH, $R^6$ = X |
| Analog (89) | $R^1$ = NH, $R^2$ = OCOR, $R^3$ = OCOR, $R^4$ = H, $R^5$ = OH, $R^6$ = H |
| Analog (90) | $R^1$ = NH, $R^2$ = OZ, $R^3$ = OZ, $R^4$ = H, $R^5$ = OH, $R^6$ = H |
| Analog (91) | $R^1$ = NH, $R^2$ = OCOR, $R^3$ = OCOR, $R^4$ = H, $R^5$ = OCOR, $R^6$ = H |
| Analog (92) | $R^1$ = NH, $R^2$ = OZ, $R^3$ = OZ, $R^4$ = H, $R^5$ = OZ, $R^6$ = H |
| Analog (93) | $R^1$ = O, $R^2$ = OCOR, $R^3$ = OCOR, $R^4$ = H, $R^5$ = OH, $R^6$ = H |
| Analog (94) | $R^1$ = O, $R^2$ = OZ, $R^3$ = OZ, $R^4$ = H, $R^5$ = OH, $R^6$ = H |
| Analog (95) | $R^1$ = O, $R^2$ = OCOR, $R^3$ = OCOR, $R^4$ = H, $R^5$ = OCOR, $R^6$ = H |
| Analog (96) | $R^1$ = O, $R^2$ = OZ, $R^3$ = OZ, $R^4$ = H, $R^5$ = OZ, $R^6$ = H |
| Analog (97) | $R^1$ = NH, $R^2$ = OH, $R^3$ = OH, $R^4$ = H, $R^5$ = OH, $R^6$ = H |
| Analog (98) | $R^1$ = O, $R^2$ = OH, $R^3$ = OH, $R^4$ = H, $R^5$ = OH, $R^6$ = H |

-continued

| | |
|---|---|
| Analog (99) | $R^1$ = NH, $R^2$ = OH, $R^3$ = OH, $R^4$ = R, $R^5$ = OH, $R^6$ = H |
| Analog (100) | $R^1$ = O, $R^2$ = OH, $R^3$ = OH, $R^4$ = R, $R^5$ = OH, $R^6$ = H |
| Analog (101) | $R^1$ = NH, $R^2$ = OCOR, $R^3$ = OCOR, $R^4$ = R, $R^5$ = OH, $R^6$ = H |
| Analog (102) | $R^1$ = NH, $R^2$ = OZ, $R^3$ = OZ, $R^4$ = R, $R^5$ = OH, $R^6$ = H |
| Analog (103) | $R^1$ = NH, $R^2$ = OCOR, $R^3$ = OCOR, $R^4$ = R, $R^5$ = OCOR, $R^6$ = H |
| Analog (104) | $R^1$ = NH, $R^2$ = OZ, $R^3$ = OZ, $R^4$ = R, $R^5$ = OZ, $R^6$ = H |
| Analog (105) | $R^1$ = O, $R^2$ = OCOR, $R^3$ = OCOR, $R^4$ = R, $R^5$ = OH$_2$, $R^6$ = H |
| Analog (106) | $R^1$ = O, $R^2$ = OZ, $R^3$ = OZ, $R^4$ = R, $R^5$ = OH$_2$, $R^6$ = H |
| Analog (107) | $R^1$ = O, $R^2$ = OCOR, $R^3$ = OCOR, $R^4$ = R, $R^5$ = OCOR, $R^6$ = H |
| Analog (108) | $R^1$ = O, $R^2$ = OZ, $R^3$ = OZ, $R^4$ = R, $R^5$ = OZ, $R^6$ = H |
| Analog (109) | $R^1$ = NH, $R^2$ = OCOR, $R^3$ = OH, $R^4$ = H, $R^5$ = OH, $R^6$ = H |
| Analog (110) | $R^1$ = NH, $R^2$ = OZ, $R^3$ = OH, $R^4$ = H, $R^5$ = OH, $R^6$ = H |
| Analog (111) | $R^1$ = O, $R^2$ = OCOR, $R^3$ = OH, $R^4$ = H, $R^5$ = OH, $R^6$ = H |
| Analog (112) | $R^1$ = O, $R^2$ = OZ, $R^3$ = OH, $R^4$ = H, $R^5$ = OH, $R^6$ = H |
| Analog (113) | $R^1$ = NH, $R^2$ = OH, $R^3$ = OCOR, $R^4$ = R, $R^5$ = OH, $R^6$ = H |
| Analog (114) | $R^1$ = NH, $R^2$ = OH, $R^3$ = OZ, $R^4$ = R, $R^5$ = OH, $R^6$ = H |
| Analog (115) | $R^1$ = O, $R^2$ = OH, $R^3$ = OCOR, $R^4$ = R, $R^5$ = OH, $R^6$ = H |
| Analog (116) | $R^1$ = O, $R^2$ = OH, $R^3$ = OZ, $R^4$ = R, $R^5$ = OH, $R^6$ = H. |

16. A method for inhibiting the proliferation of cancer cells wherein said method comprises administering to said cells a cancer cell proliferation inhibiting amount of a compound having the following structure:

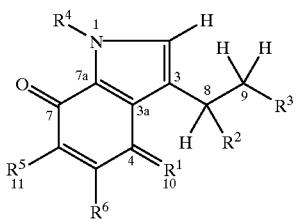

wherein $R^1$ is NH or O;
$R^2$ is OZ;
$R^3$ is OZ;
$R^4$ is be H or R;
$R^5$ is NH$_2$, NR$_2$, or OZ; and
$R^6$ is H or X;
wherein Z is selected from the group consisting of H, R, COR, mesyl, tosyl, glutamyl, succinyl, and malonyl;
R is selected from the group consisting of C1 to C8 alkyl, phenyl, and benzyl; and
X is Cl, Br, or I.

17. The method, according to claim 16, wherein $R^1$ is NH; $R^2$ is OH; $R^3$ is OH; $R^4$ is H; $R^5$ is NH$_2$ and $R^6$ is Cl.

18. The method, according to claim 16, wherein $R^1$ is NH; $R^2$ is OCOR; $R^3$ is OCOR; $R^4$ is H; $R^5$ is NH$_2$; and $R^6$ is Cl.

19. The method, according to claim 16, wherein $R^1$ is O; $R^2$ is OH; $R^3$ is OH; $R^4$ is H; $R^5$ is NH$_2$; and $R^6$ is Cl.

20. The method, according to claim 16, wherein $R^1$ is O; $R^2$ is OCOR; $R^3$ is OCOR; $R^4$ is H; $R^5$ is NH$_2$; and $R^6$ is Cl.

21. The method, according to claim 16, wherein said compound is selected from the group consisting of:

| | |
|---|---|
| Analog (5) | $R^1$ = NH, $R^2$ = OH, $R^3$ = OCOR, $R^4$ = H, $R^5$ = NH$_2$, $R^6$ = X |
| Analog (6) | $R^1$ = NH, $R^2$ = OH, $R^3$ = OZ, $R^4$ = H, $R^5$ = NH$_2$, $R^6$ = X |
| Analog (7) | $R^1$ = NH, $R^2$ = OCOR, $R^3$ = OH, $R^4$ = H, $R^5$ = NH$_2$, $R^6$ = X |
| Analog (8) | $R^1$ = NH, $R^2$ = OZ, $R^3$ = OH, $R^4$ = H, $R^5$ = NH$_2$, $R^6$ = X |
| Analog (9) | $R^1$ = O, $R^2$ = OH, $R^3$ = OCOR, $R^4$ = H, $R^5$ = NH$_2$, $R^6$ = X |
| Analog (10) | $R^1$ = O, $R^2$ = OH, $R^3$ = OZ, $R^4$ = H, $R^5$ = NH$_2$, $R^6$ = X |

-continued

| | |
|---|---|
| Analog (11) | $R^1$ = O, $R^2$ = OCOR, $R^3$ = OH, $R^4$ = H, $R^5$ = NH$_2$, $R^6$ = X |
| Analog (12) | $R^1$ = O, $R^2$ = OZ, $R^3$ = OH, $R^4$ = H, $R^5$ = NH$_2$, $R^6$ = X |
| Analog (13) | $R^1$ = NH, $R^2$ = OH, $R^3$ = OH, $R^4$ = R, $R^5$ = NH$_2$, $R^6$ = X |
| Analog (14) | $R^1$ = O, $R^2$ = OH, $R^3$ = OH, $R^4$ = R, $R^5$ = NH$_2$, $R^6$ = X |
| Analog (15) | $R^1$ = NH, $R^2$ = OH, $R^3$ = OH, $R^4$ = H, $R^5$ = NR$_2$, $R^6$ = X |
| Analog (16) | $R^1$ = O, $R^2$ = OH, $R^3$ = OH, $R^4$ = H, $R^5$ = NR$_2$, $R^6$ = X |
| Analog (17) | $R^1$ = NH, $R^2$ = OH, $R^3$ = OH, $R^4$ = R, $R^5$ = NR$_2$, $R^6$ = X |
| Analog (18) | $R^1$ = O, $R^2$ = OH, $R^3$ = OH, $R^4$ = R, $R^5$ = NR$_2$, $R^6$ = X |
| Analog (19) | $R^1$ = NH, $R^2$ = OCOR, $R^3$ = OCOR, $R^4$ = R, $R^5$ = NH$_2$, $R^6$ = X |
| Analog (20) | $R^1$ = NH, $R^2$ = OZ, $R^3$ = OZ, $R^4$ = R, $R^5$ = NH$_2$, $R^6$ = X |
| Analog (21) | $R^1$ = O, $R^2$ = OCOR, $R^3$ = OCOR, $R^4$ = R, $R^5$ = NH$_2$, $R^6$ = X |
| Analog (22) | $R^1$ = O, $R^2$ = OZ, $R^3$ = OZ, $R^4$ = R, $R^5$ = NH$_2$, $R^6$ = X |
| Analog (23) | $R^1$ = NH, $R^2$ = OCOR, $R^3$ = OH, $R^4$ = H, $R^5$ = NR$_2$, $R^6$ = X |
| Analog (24) | $R^1$ = NH, $R^2$ = OZ, $R^3$ = OH, $R^4$ = H, $R^5$ = NR$_2$, $R^6$ = X |
| Analog (25) | $R^1$ = O, $R^2$ = OCOR, $R^3$ = OH, $R^4$ = H, $R^5$ = NR$_2$, $R^6$ = X |
| Analog (26) | $R^1$ = O, $R^2$ = OZ, $R^3$ = OH, $R^4$ = H, $R^5$ = NR$_2$, $R^6$ = X |
| Analog (27) | $R^1$ = NH, $R^2$ = OH, $R^3$ = OCOR, $R^4$ = R, $R^5$ = NR$_2$, $R^6$ = X |
| Analog (28) | $R^1$ = NH, $R^2$ = OH, $R^3$ = OZ, $R^4$ = R, $R^5$ = NR$_2$, $R^6$ = X |
| Analog (29) | $R^1$ = O, $R^2$ = OH, $R^3$ = OCOR, $R^4$ = R, $R^5$ = NR$_2$, $R^6$ = X |
| Analog (30) | $R^1$ = O, $R^2$ = OH, $R^3$ = OZ, $R^4$ = R, $R^5$ = NR$_2$, $R^6$ = X |
| Analog (31) | $R^1$ = NH, $R^2$ = OCOR, $R^3$ = OCOR, $R^4$ = H, $R^5$ = NH$_2$, $R^6$ = H |
| Analog (32) | $R^1$ = NH, $R^2$ = OZ, $R^3$ = OZ, $R^4$ = H, $R^5$ = NH$_2$, $R^6$ = H |
| Analog (33) | $R^1$ = O, $R^2$ = OCOR, $R^3$ = OCOR, $R^4$ = H; $R^5$ = NH$_2$, $R^6$ = H |
| Analog (34) | $R^1$ = O, $R^2$ = OZ, $R^3$ = OZ, $R^4$ = H, $R^5$ = NH$_2$, $R^6$ = H |
| Analog (35) | $R^1$ = NH, $R^2$ = OH, $R^3$ = OCOR, $R^4$ = H, $R^5$ = NH$_2$, $R^6$ = H |
| Analog (36) | $R^1$ = NH, $R^2$ = OH, $R^3$ = OZ, $R^4$ = H, $R^5$ = NH$_2$, $R^6$ = H |
| Analog (37) | $R^1$ = NH, $R^2$ = OCOR, $R^3$ = OH, $R^4$ = H, $R^5$ = NH$_2$, $R^6$ = H |
| Analog (38) | $R^1$ = NH, $R^2$ = OZ, $R^3$ = OH, $R^4$ = H, $R^5$ = NH$_2$, $R^6$ = H |
| Analog (39) | $R^1$ = O, $R^2$ = OH, $R^3$ = OCOR, $R^4$ = H, $R^5$ = NH$_2$, $R^6$ = H |
| Analog (40) | $R^1$ = O, $R^2$ = OH, $R^3$ = OZ, $R^4$ = H, $R^5$ = NH$_2$, $R^6$ = H |
| Analog (41) | $R^1$ = O, $R^2$ = OCOR, $R^3$ = OH, $R^4$ = H, $R^5$ = NH$_2$, $R^6$ = H |
| Analog (42) | $R^1$ = O, $R^2$ = OZ, $R^3$ = OH, $R^4$ = H, $R^5$ = NH$_2$, $R^6$ = H |
| Analog (43) | $R^1$ = NH, $R^2$ = OH, $R^3$ = OH, $R^4$ = R, $R^5$ = NH$_2$, $R^6$ = H |
| Analog (44) | $R^1$ = O, $R^2$ = OH, $R^3$ = OH, $R^4$ = R, $R^5$ = NH$_2$, $R^6$ = H |
| Analog (45) | $R^1$ = NH, $R^2$ = OH, $R^3$ = OH, $R^4$ = H, $R^5$ = NR$_2$, $R^6$ = H |
| Analog (46) | $R^1$ = O, $R^2$ = OH, $R^3$ = OH, $R^4$ = H, $R^5$ = NR$_2$, $R^6$ = H |
| Analog (47) | $R^1$ = NH, $R^2$ = OH, $R^3$ = OH, $R^4$ = R, $R^5$ = NR$_2$, $R^6$ = H |
| Analog (48) | $R^1$ = O, $R^2$ = OH, $R^3$ = OH, $R^4$ = R, $R^5$ = NR$_2$, $R^6$ = H |
| Analog (49) | $R^1$ = NH, $R^2$ = OCOR, $R^3$ = OCOR, $R^4$ = R, $R^5$ = NH$_2$, $R^6$ = H |
| Analog (50) | $R^1$ = NH, $R^2$ = OZ, $R^3$ = OZ, $R^4$ = R, $R^5$ = NH$_2$, $R^6$ = H |
| Analog (51) | $R^1$ = O, $R^2$ = OCOR, $R^3$ = OCOR, $R^4$ = R, $R^5$ = NH$_2$, $R^6$ = H |
| Analog (52) | $R^1$ = O, $R^2$ = OZ, $R^3$ = OZ, $R^4$ = R, $R^5$ = NH$_2$, $R^6$ = H |
| Analog (53) | $R^1$ = NH, $R^2$ = OCOR, $R^3$ = OH, $R^4$ = H, $R^5$ = NR$_2$, $R^6$ = H |
| Analog (54) | $R^1$ = NH, $R^2$ = OZ, $R^3$ = OH, $R^4$ = H, $R^5$ = NR$_2$, $R^6$ = H |

-continued

| | |
|---|---|
| Analog (55) | $R^1$ = O, $R^2$ = OCOR, $R^3$ = OH, $R^4$ = H, $R^5$ = $NR_2$, $R^6$ = H |
| Analog (56) | $R^1$ = O, $R^2$ = OZ, $R^3$ = OH, $R^4$ = H, $R^5$ = $NR_2$, $R^6$ = H |
| Analog (57) | $R^1$ = NH, $R^2$ = OH, $R^3$ = OCOR, $R^4$ = R, $R^5$ = $NR_2$, $R^6$ = H |
| Analog (58) | $R^1$ = NH, $R^2$ = OH, $R^3$ = OZ, $R^4$ = R, $R^5$ = $NR_2$, $R^6$ = H |
| Analog (59) | $R^1$ = O, $R^2$ = OH, $R^3$ = OCOR, $R^4$ = R, $R^5$ = $NR_2$, $R^6$ = H |
| Analog (60) | $R^1$ = O, $R^2$ = OH, $R^3$ = OZ, $R^4$ = R, $R^5$ = $NR_2$, $R^6$ = H |
| Analog (61) | $R^1$ = NH, $R^2$ = OCOR, $R^3$ = OCOR, $R^4$ = H, $R^5$ = OH, $R^6$ = X |
| Analog (62) | $R^1$ = NH, $R^2$ = OZ, $R^3$ = OZ, $R^4$ = H, $R^5$ = OH, $R^6$ = X |
| Analog (63) | $R^1$ = NH, $R^2$ = OCOR, $R^3$ = OCOR, $R^4$ = H, $R^5$ = OCOR, $R^6$ = X |
| Analog (64) | $R^1$ = NH, $R^2$ = OZ, $R^3$ = OZ, $R^4$ = H, $R^5$ = OZ, $R^6$ = X |
| Analog (65) | $R^1$ = O, $R^2$ = OCOR, $R^3$ = OCOR, $R^4$ = H, $R^5$ = OH, $R^6$ = X |
| Analog (66) | $R^1$ = O, $R^2$ = OZ, $R^3$ = OZ, $R^4$ = H, $R^5$ = OH, $R^6$ = X |
| Analog (67) | $R^1$ = O, $R^2$ = OCOR, $R^3$ = OCOR, $R^4$ = H, $R^5$ = OCOR, $R^6$ = X |
| Analog (68) | $R^1$ = O, $R^2$-OZ, $R^3$ = OZ, $R^4$ = H, $R^5$ = OZ, $R^6$ = X |
| Analog (69) | $R^1$ = NH, $R^2$ = OH, $R^3$ = OH, $R^4$ = H, $R^5$ = OH, $R^6$ = X |
| Analog (70) | $R^1$ = O, $R^2$ = OH, $R^3$ = OH, $R^4$ = H, $R^5$ = OH, $R^6$ = X |
| Analog (71) | $R^1$ = NH, $R^2$ = OH, $R^3$ = OH, $R^4$ = R, $R^5$ = OH, $R^6$ = X |
| Analog (72) | $R^1$ = O, $R^2$ = OH, $R^3$ = OH, $R^4$ = R, $R^5$ = OH, $R^6$ = X |
| Analog (73) | $R^1$ = NH, $R^2$ = OCOR, $R^3$ = OCOR, $R^4$ = R, $R^5$ = OH, $R^6$ = X |
| Analog (74) | $R^1$ = NH, $R^2$ = OZ, $R^3$ = OZ, $R^4$ = R, $R^5$ = OH, $R^6$ = X |
| Analog (75) | $R^1$ = NH, $R^2$ = OCOR, $R^3$ = OCOR, $R^4$ = R, $R^5$ = OCOR, $R^6$ = X |
| Analog (76) | $R^1$ = NH, $R^2$ = OZ, $R^3$ = OZ, $R^4$ = R, $R^5$ = OZ, $R^6$ = X |
| Analog (77) | $R^1$ = O, $R^2$ = OCOR, $R^3$ = OCOR, $R^4$ = R, $R^5$ = $OH_2$, $R^6$ = X |
| Analog (78) | $R^1$ = O, $R^2$ = OZ, $R^3$ = OZ, $R^4$ = R, $R^5$ = $OH_2$, $R^6$ = X |
| Analog (79) | $R^1$ = O, $R^2$ = OCOR, $R^3$ = OCOR, $R^4$ = R, $R^5$ = OCOR, $R^6$ = X |
| Analog (80) | $R^1$ = O, $R^2$ = OZ, $R^3$ = OZ, $R^4$ = R, $R^5$ = OZ, $R^6$ = X |
| Analog (81) | $R^1$ = NH, $R^2$ = OCOR, $R^3$ = OH, $R^4$ = H, $R^5$ = OH, $R^6$ = X |
| Analog (82) | $R^1$ = NH, $R^2$ = OZ, $R^3$ = OH, $R^4$ = H, $R^5$ = OH, $R^6$ = X |
| Analog (83) | $R^1$ = O, $R^2$ = OCOR, $R^3$ = OH, $R^4$ = H, $R^5$ = OH, $R^6$ = X |
| Analog (84) | $R^1$ = O, $R^2$ = OZ, $R^3$ = OH, $R^4$ = H, $R^5$ = OH, $R^6$ = X |
| Analog (85) | $R^1$ = NH, $R^2$ = OH, $R^3$ = OCOR, $R^4$ = H, $R^5$ = OH, $R^6$ = X |
| Analog (86) | $R^1$ = NH, $R^2$ = OH, $R^3$ = OZ, $R^4$ = H, $R^5$ = OH, $R^6$ = X |
| Analog (87) | $R^1$ = O, $R^2$ = OH, $R^3$ = OCOR, $R^4$ = H, $R^5$ = OH, $R^6$ = X |
| Analog (88) | $R^1$ = O, $R^2$ = OH, $R^3$ = OZ, $R^4$ = H, $R^5$ = OH, $R^6$ = X |
| Analog (89) | $R^1$ = NH, $R^2$ = OCOR, $R^3$ = OCOR, $R^4$ = H, $R^5$ = OH, $R^6$ = H |
| Analog (90) | $R^1$ = NH, $R^2$ = OZ, $R^3$ = OZ, $R^4$ = H, $R^5$ = OH, $R^6$ = H |
| Analog (91) | $R^1$ = NH, $R^2$ = OCOR, $R^3$ = OCOR, $R^4$ = H, $R^5$ = OCOR, $R^6$ = H |
| Analog (92) | $R^1$ = NH, $R^2$ = OZ, $R^3$ = OZ, $R^4$ = H, $R^5$ = OZ, $R^6$ = H |
| Analog (93) | $R^1$ = O, $R^2$ = OCOR, $R^3$ = OCOR, $R^4$ = H, $R^5$ = OH, $R^6$ = H |
| Analog (94) | $R^1$ = O, $R^2$ = OZ, $R^3$ = OZ, $R^4$ = H, $R^5$ = OH, $R^6$ = H |
| Analog (95) | $R^1$ = O, $R^2$ = OCOR, $R^3$ = OCOR, $R^4$ = H, $R^5$ = OCOR, $R^6$ = H |
| Analog (96) | $R^1$ = O, $R^2$ = OZ, $R^3$ = OZ, $R^4$ = H, $R^5$ = OZ, $R^6$ = H |
| Analog (97) | $R^1$ = NH, $R^2$ = OH, $R^3$ = OH, $R^4$ = H, $R^5$ = OH, $R^6$ = H |
| Analog (98) | $R^1$ = O, $R^2$ = OH, $R^3$ = OH, $R^4$ = H, $R^5$ = OH, $R^6$ = H |
| Analog (99) | $R^1$ = NH, $R^2$ = OH, $R^3$ = OH, $R^4$ = R, $R^5$ = OH, $R^6$ = H |
| Analog (100) | $R^1$ = O, $R^2$ = OH, $R^3$ = OH, $R^4$ = R, $R^5$ = OH, $R^6$ = H |
| Analog (101) | $R^1$ = NH, $R^2$ = OCOR, $R^3$ = OCOR, $R^4$ = R, $R^5$ = OH, $R^6$ = H |
| Analog (102) | $R^1$ = NH, $R^2$ = OZ, $R^3$ = OZ, $R^4$ = R, $R^5$ = OH, $R^6$ = H |
| Analog (103) | $R^1$ = NH, $R^2$ = OCOR, $R^3$ = OCOR, $R^4$ = R, $R^5$ = OCOR, $R^6$ = H |
| Analog (104) | $R^1$ = NH, $R^2$ = OZ, $R^3$ = OZ, $R^4$ = R, $R^5$ = OZ, $R^6$ = H |
| Analog (105) | $R^1$ = O, $R^2$ = OCOR, $R^3$ = OCOR, $R^4$ = R, $R^5$ = $OH_2$, $R^6$ = H |
| Analog (106) | $R^1$ = O, $R^2$ = OZ, $R^3$ = OZ, $R^4$ = R, $R^5$ = $OH_2$, $R^6$ = H |
| Analog (107) | $R^1$ = O, $R^2$ = OCOR, $R^3$ = OCOR, $R^4$ = R, $R^5$ = OCOR, $R^6$ = H |
| Analog (108) | $R^1$ = O, $R^2$ = OZ, $R^3$ = OZ, $R^4$ = R, $R^5$ = OZ, $R^6$ = H |
| Analog (109) | $R^1$ = NH, $R^2$ = OCOR, $R^3$ = OH, $R^4$ = H, $R^5$ = OH, $R^6$ = H |
| Analog (110) | $R^1$ = NH, $R^2$ = OZ, $R^3$ = OH, $R^4$ = H, $R^5$ = OH, $R^6$ = H |
| Analog (111) | $R^1$ = O, $R^2$ = OCOR, $R^3$ = OH, $R^4$ = H, $R^5$ = OH, $R^6$ = H |
| Analog (112) | $R^1$ = O, $R^2$ = OZ, $R^3$ = OH, $R^4$ = H, $R^5$ = OH, $R^6$ = H |
| Analog (113) | $R^1$ = NH, $R^2$ = OH, $R^3$ = OCOR, $R^4$ = R, $R^5$ = OH, $R^6$ = H |
| Analog (114) | $R^1$ = NH, $R^2$ = OH, $R^3$ = OZ, $R^4$ = R, $R^5$ = OH, $R^6$ = H |
| Analog (115) | $R^1$ = O, $R^2$ = OH, $R^3$ = OCOR, $R^4$ = R, $R^5$ = OH, $R^6$ = H |
| Analog (116) | $R^1$ = O, $R^2$ = OH, $R^3$ = OZ, $R^4$ = R, $R^5$ = OH, $R^6$ = H. |

22. The method, according to claim 16, wherein said cancer cells are selected from the group consisting of cancer cells of the breast, colon, renal, ovarian, prostate, central nervous system (CNS), lung, leukemia and melanoma.

23. A method for modulating the immune response of an animal wherein said method comprises administering to said animal an effective amount of a compound having the following structure:

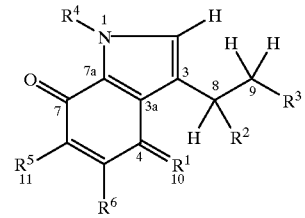

wherein $R^1$ is NH or O;
  $R^2$ is OZ;
  $R^3$ is OZ;
  $R^4$ is H or R;
  $R^5$ is $NH_2$, $NR_2$, or OZ; and
  $R^6$ is H or X;
wherein Z is selected from the group consisting of H, R, COR, mesyl, tosyl, glutamyl, succinyl, and malonyl;
R is selected from the group consisting of C1 to C8 alkyl, phenyl, and benzyl; and
X is Cl, Br, or I.

24. The method, according to claim 23, wherein said immune modulation is immune suppression.

25. The compound, according to claim 23, wherein $R^1$ is NH; $R^2$ is OH; $R^3$ is OH; $R^4$ is H; $R^5$ is $NH_2$ and $R^6$ is Cl.

26. The compound, according to claim 23, wherein $R^1$ is NH; $R^2$ is OCOR; $R^3$ is OCOR; $R^4$ is H; $R^5$ is $NH_2$; and $R^6$ is Cl.

27. The compound, according to claim 23, wherein $R^1$ is O; $R^2$ is OH; $R^3$ is OH; $R^4$ is H; $R^5$ is $NH_2$; and $R^6$ is Cl.

28. The compound, according to claim 23, wherein $R^1$ is O; $R^2$ is OCOR; $R^3$ is OCOR; $R^4$ is H; $R^5$ is $NH_2$; and $R^6$ is Cl.

29. The compound, according to claim 23, wherein said compound is selected from the group consisting of:

| | |
|---|---|
| Analog (5) | $R^1$ = NH, $R^2$ = OH, $R^3$ = OCOR, $R^4$ = H, $R^5$ = $NH_2$, $R^6$ = X |
| Analog (6) | $R^1$ = NH, $R^2$ = OH, $R^3$ = OZ, $R^4$ = H, $R^5$ = $NH_2$, $R^6$ = X |
| Analog (7) | $R^1$ = NH, $R^2$ = OCOR, $R^3$ = OH, $R^4$ = H, $R^5$ = $NH_2$, $R^6$ = X |
| Analog (8) | $R^1$ = NH, $R^2$ = OZ, $R^3$ = OH, $R^4$ = H, $R^5$ = $NH_2$, $R^6$ = X |
| Analog (9) | $R^1$ = O, $R^2$ = OH, $R^3$ = OCOR, $R^4$ = H, $R^5$ = $NH_2$, $R^6$ = X |
| Analog (10) | $R^1$ = O, $R^2$ = OH, $R^3$ = OZ, $R^4$ = H, $R^5$ = $NH_2$, $R^6$ = X |
| Analog (11) | $R^1$ = O, $R^2$ = OCOR, $R^3$ = OH, $R^4$ = H, $R^5$ = $NH_2$, $R^6$ = X |
| Analog (12) | $R^1$ = O, $R^2$ = OZ, $R^3$ = OH, $R^4$ = H, $R^5$ = $NH_2$, $R^6$ = X |
| Analog (13) | $R^1$ = NH, $R^2$ = OH, $R^3$ = OH, $R^4$ = R, $R^5$ = $NH_2$, $R^6$ = X |
| Analog (14) | $R^1$ = O, $R^2$ = OH, $R^3$ = OH, $R^4$ = R, $R^5$ = $NH_2$, $R^6$ = X |
| Analog (15) | $R^1$ = NH, $R^2$ = OH, $R^3$ = OH, $R^4$ = H, $R^5$ = $NR_2$, $R^6$ = X |
| Analog (16) | $R^1$ = O, $R^2$ = OH, $R^3$ = OH, $R^4$ = H, $R^5$ = $NR_2$, $R^6$ = X |

-continued

| | |
|---|---|
| Analog (17) | $R^1$ = NH, $R^2$ = OH, $R^3$ = OH, $R^4$ = R, $R^5$ = $NR_2$, $R^6$ = X |
| Analog (18) | $R^1$ = O, $R^2$ = OH, $R^3$ = OH, $R^4$ = R, $R^5$ = $NR_2$, $R^6$ = X |
| Analog (19) | $R^1$ = NH, $R^2$ = OCOR, $R^3$ = OCOR, $R^4$ = R, $R^5$ = $NH_2$, $R^6$ = X |
| Analog (20) | $R^1$ = NH, $R^2$ = OZ, $R^3$ = OZ, $R^4$ = R, $R^5$ = $NH_2$, $R^6$ = X |
| Analog (21) | $R^1$ = O, $R^2$ = OCOR, $R^3$ = OCOR, $R^4$ = R, $R^5$ = $NH_2$, $R^6$ = X |
| Analog (22) | $R^1$ = O, $R^2$ = OZ, $R^3$ = OZ, $R^4$ = R, $R^5$ = $NH_2$, $R^6$ = X |
| Analog (23) | $R^1$ = NH, $R^2$ = OCOR, $R^3$ = OH, $R^4$ = H, $R^5$ = $NR_2$, $R^6$ = X |
| Analog (24) | $R^1$ = NH, $R^2$ = OZ, $R^3$ = OH, $R^4$ = H, $R^5$ = $NR_2$, $R^6$ = X |
| Analog (25) | $R^1$ = O, $R^2$ = OCOR, $R^3$ = OH, $R^4$ = H, $R^5$ = $NR_2$, $R^6$ = X |
| Analog (26) | $R^1$ = O, $R^2$ = OZ, $R^3$ = OH, $R^4$ = H, $R^5$ = $NR_2$, $R^6$ = X |
| Analog (27) | $R^1$ = NH, $R^2$ = OH, $R^3$ = OCOR, $R^4$ = R, $R^5$ = $NR_2$, $R^6$ = X |
| Analog (28) | $R^1$ = NH, $R^2$ = OH, $R^3$ = OZ, $R^4$ = R, $R^5$ = $NR_2$, $R^6$ = X |
| Analog (29) | $R^1$ = NH, $R^2$ = OH, $R^3$ = OCOR, $R^4$ = R, $R^5$ = $NR_2$, $R^6$ = X |
| Analog (30) | $R^1$ = O, $R^2$ = OH, $R^3$ = OZ, $R^4$ = R, $R^5$ = $NR_2$, $R^6$ = X |
| Analog (31) | $R^1$ = NH, $R^2$ = OCOR, $R^3$ = OCOR, $R^4$ = H, $R^5$ = $NH_2$, $R^6$ = H |
| Analog (32) | $R^1$ = NH, $R^2$ = OZ, $R^3$ = OZ, $R^4$ = H, $R^5$ = $NH_2$, $R^6$ = H |
| Analog (33) | $R^1$ = O, $R^2$ = OCOR, $R^3$ = OCOR, $R^4$ = H; $R^5$ = $NH_2$, $R^6$ = H |
| Analog (34) | $R^1$ = O, $R^2$ = OZ, $R^3$ = OZ, $R^4$ = H, $R^5$ = $NH_2$, $R^6$ = H |
| Analog (35) | $R^1$ = NH, $R^2$ = OH, $R^3$ = OCOR, $R^4$ = H, $R^5$ = $NH_2$, $R^6$ = H |
| Analog (36) | $R^1$ = NH, $R^2$ = OH, $R^3$ = OH, $R^4$ = H, $R^5$ = $NH_2$, $R^6$ = H |
| Analog (37) | $R^1$ = NH, $R^2$ = OCOR, $R^3$ = OH, $R^4$ = H, $R^5$ = $NH_2$, $R^6$ = H |
| Analog (38) | $R^1$ = NH, $R^2$ = OZ, $R^3$ = OH, $R^4$ = H, $R^5$ = $NH_2$, $R^6$ = H |
| Analog (39) | $R^1$ = O, $R^2$ = OH, $R^3$ = OCOR, $R^4$ = H, $R^5$ = $NH_2$, $R^6$ = H |
| Analog (40) | $R^1$ = O, $R^2$ = OH, $R^3$ = OZ, $R^4$ = H, $R^5$ = $NH_2$, $R^6$ = H |
| Analog (41) | $R^1$ = O, $R^2$ = OCOR, $R^3$ = OH, $R^4$ = H, $R^5$ = $NH_2$, $R^6$ = H |
| Analog (42) | $R^1$ = O, $R^2$ = OZ, $R^3$ = OH, $R^4$ = H, $R^5$ = $NH_2$, $R^6$ = H |
| Analog (43) | $R^1$ = NH, $R^2$ = OH, $R^3$ = OH, $R^4$ = R, $R^5$ = $NH_2$, $R^6$ = H |
| Analog (44) | $R^1$ = O, $R^2$ = OH, $R^3$ = OH, $R^4$ = R, $R^5$ = $NH_2$, $R^6$ = H |
| Analog (45) | $R^1$ = NH, $R^2$ = OH, $R^3$ = OH, $R^4$ = H, $R^5$ = $NR_2$, $R^6$ = H |
| Analog (46) | $R^1$ = O, $R^2$ = OH, $R^3$ = OH, $R^4$ = H, $R^5$ = $NR_2$, $R^6$ = H |
| Analog (47) | $R^1$ = NH, $R^2$ = OH, $R^3$ = OH, $R^4$ = R, $R^5$ = $NR_2$, $R^6$ = H |
| Analog (48) | $R^1$ = O, $R^2$ = OH, $R^3$ = OH, $R^4$ = R, $R^5$ = $NR_2$, $R^6$ = H |
| Analog (49) | $R^1$ = NH, $R^2$ = OCOR, $R^3$ = OCOR, $R^4$ = R, $R^5$ = $NH_2$, $R^6$ = H |
| Analog (50) | $R^1$ = NH, $R^2$ = OZ, $R^3$ = OZ, $R^4$ = R, $R^5$ = $NH_2$, $R^6$ = H |
| Analog (51) | $R^1$ = O, $R^2$ = OCOR, $R^3$ = OCOR, $R^4$ = R, $R^5$ = $NH_2$, $R^6$ = H |
| Analog (52) | $R^1$ = O, $R^2$ = OZ, $R^3$ = OZ, $R^4$ = R, $R^5$ = $NH_2$, $R^6$ = H |
| Analog (53) | $R^1$ = NH, $R^2$ = OCOR, $R^3$ = OH, $R^4$ = H, $R^5$ = $NR_2$, $R^6$ = H |
| Analog (54) | $R^1$ = NH, $R^2$ = OZ, $R^3$ = OH, $R^4$ = H, $R^5$ = $NR_2$, $R^6$ = H |
| Analog (55) | $R^1$ = O, $R^2$ = OCOR, $R^3$ = OH, $R^4$ = H, $R^5$ = $NR_2$, $R^6$ = H |
| Analog (56) | $R^1$ = O, $R^2$ = OZ, $R^3$ = OH, $R^4$ = H, $R^5$ = $NR_2$, $R^6$ = H |
| Analog (57) | $R^1$ = NH, $R^2$ = OH, $R^3$ = OCOR, $R^4$ = R, $R^5$ = $NR_2$, $R^6$ = H |
| Analog (58) | $R^1$ = NH, $R^2$ = OH, $R^3$ = OZ, $R^4$ = R, $R^5$ = $NR_2$, $R^6$ = H |
| Analog (59) | $R^1$ = O, $R^2$ = OH, $R^3$ = OCOR, $R^4$ = R, $R^5$ = $NR_2$, $R^6$ = H |
| Analog (60) | $R^1$ = O, $R^2$ = OH, $R^3$ = OZ, $R^4$ = R, $R^5$ = $NR_2$, $R^6$ = H |
| Analog (61) | $R^1$ = NH, $R^2$ = OCOR, $R^3$ = OCOR, $R^4$ = H, $R^5$ = OH, $R^6$ = X |
| Analog (62) | $R^1$ = NH, $R^2$ = OZ, $R^3$ = OZ, $R^4$ = H, $R^5$ = OH, $R^6$ = X |
| Analog (63) | $R^1$ = NH, $R^2$ = OCOR, $R^3$ = OCOR, $R^4$ = H, $R^5$ = OCOR, $R^6$ = X |
| Analog (64) | $R^1$ = NH, $R^2$ = OZ, $R^3$ = OZ, $R^4$ = H, $R^5$ = OZ, $R^6$ = X |
| Analog (65) | $R^1$ = O, $R^2$ = OCOR, $R^3$ = OCOR, $R^4$ = H, $R^5$ = OH, $R^6$ = X |
| Analog (66) | $R^1$ = O, $R^2$ = OZ, $R^3$ = OZ, $R^4$ = H, $R^5$ = OH, $R^6$ = X |
| Analog (67) | $R^1$ = O, $R^2$ = OCOR, $R^3$ = OCOR, $R^4$ = H, $R^5$ = OCOR, $R^6$ = X |
| Analog (68) | $R^1$ = O, $R^2$ = OZ, $R^3$ = OZ, $R^4$ = H, $R^5$ = OZ, $R^6$ = X |
| Analog (69) | $R^1$ = NH, $R^2$ = OH, $R^3$ = OH, $R^4$ = H, $R^5$ = OH, $R^6$ = X |
| Analog (70) | $R^1$ = O, $R^2$ = OH, $R^3$ = OH, $R^4$ = H, $R^5$ = OH, $R^6$ = X |
| Analog (71) | $R^1$ = NH, $R^2$ = OH, $R^3$ = OH, $R^4$ = R, $R^5$ = OH, $R^6$ = X |
| Analog (72) | $R^1$ = O, $R^2$ = OH, $R^3$ = OH, $R^4$ = R, $R^5$ = OH, $R^6$ = X |
| Analog (73) | $R^1$ = NH, $R^2$ = OCOR, $R^3$ = OCOR, $R^4$ = R, $R^5$ = OH, $R^6$ = X |
| Analog (74) | $R^1$ = NH, $R^2$ = OZ, $R^3$ = OZ, $R^4$ = R, $R^5$ = OH, $R^6$ = X |
| Analog (75) | $R^1$ = NH, $R^2$ = OCOR, $R^3$ = OCOR, $R^4$ = R, $R^5$ = OCOR, $R^6$ = X |
| Analog (76) | $R^1$ = NH, $R^2$ = OZ, $R^3$ = OZ, $R^4$ = R, $R^5$ = OZ, $R^6$ = X |
| Analog (77) | $R^1$ = O, $R^2$ = OCOR, $R^3$ = OCOR, $R^4$ = R, $R^5$ = $OH_2$, $R^6$ = X |
| Analog (78) | $R^1$ = O, $R^2$ = OZ, $R^3$ = OZ, $R^4$ = R, $R^5$ = $OH_2$, $R^6$ = X |
| Analog (79) | $R^1$ = O, $R^2$ = OCOR, $R^3$ = OCOR, $R^4$ = R, $R^5$ = OCOR, $R^6$ = X |
| Analog (80) | $R^1$ = O, $R^2$ = OZ, $R^3$ = OZ, $R^4$ = R, $R^5$ = OZ, $R^6$ = X |
| Analog (81) | $R^1$ = NH, $R^2$ = OCOR, $R^3$ = OH, $R^4$ = H, $R^5$ = OH, $R^6$ = X |
| Analog (82) | $R^1$ = NH, $R^2$ = OZ, $R^3$ = OH, $R^4$ = H, $R^5$ = OH, $R^6$ = X |
| Analog (83) | $R^1$ = O, $R^2$ = OCOR, $R^3$ = OH, $R^4$ = H, $R^5$ = OH, $R^6$ = X |
| Analog (84) | $R^1$ = O, $R^2$ = OZ, $R^3$ = OH, $R^4$ = H, $R^5$ = OH, $R^6$ = X |
| Analog (85) | $R^1$ = NH, $R^2$ = OH, $R^3$ = OCOR, $R^4$ = R, $R^5$ = OH, $R^6$ = X |
| Analog (86) | $R^1$ = NH, $R^2$ = OH, $R^3$ = OZ, $R^4$ = R, $R^5$ = OH, $R^6$ = X |
| Analog (87) | $R^1$ = O, $R^2$ = OH, $R^3$ = OCOR, $R^4$ = R, $R^5$ = OH, $R^6$ = X |
| Analog (88) | $R^1$ = O, $R^2$ = OH, $R^3$ = OZ, $R^4$ = R, $R^5$ = OH, $R^6$ = X |
| Analog (89) | $R^1$ = NH, $R^2$ = OCOR, $R^3$ = OCOR, $R^4$ = H, $R^5$ = OH, $R^6$ = H |
| Analog (90) | $R^1$ = NH, $R^2$ = OZ, $R^3$ = OZ, $R^4$ = H, $R^5$ = OH, $R^6$ = H |
| Analog (91) | $R^1$ = NH, $R^2$ = OCOR, $R^3$ = OCOR, $R^4$ = H, $R^5$ = OCOR, $R^6$ = H |
| Analog (92) | $R^1$ = NH, $R^2$ = OZ, $R^3$ = OZ, $R^4$ = H, $R^5$ = OZ, $R^6$ = H |
| Analog (93) | $R^1$ = O, $R^2$ = OCOR, $R^3$ = OCOR, $R^4$ = H, $R^5$ = OH, $R^6$ = H |
| Analog (94) | $R^1$ = O, $R^2$ = OZ, $R^3$ = OZ, $R^4$ = H, $R^5$ = OH, $R^6$ = H |
| Analog (95) | $R^1$ = O, $R^2$ = OCOR, $R^3$ = OCOR, $R^4$ = H, $R^5$ = OCOR, $R^6$ = H |
| Analog (96) | $R^1$ = O, $R^2$ = OZ, $R^3$ = OZ, $R^4$ = H, $R^5$ = OZ, $R^6$ = H |
| Analog (97) | $R^1$ = NH, $R^2$ = OH, $R^3$ = OH, $R^4$ = H, $R^5$ = OH, $R^6$ = H |
| Analog (98) | $R^1$ = O, $R^2$ = OH, $R^3$ = OH, $R^4$ = H, $R^5$ = OH, $R^6$ = H |
| Analog (99) | $R^1$ = NH, $R^2$ = OH, $R^3$ = OH, $R^4$ = R, $R^5$ = OH, $R^6$ = H |
| Analog (100) | $R^1$ = O, $R^2$ = OH, $R^3$ = OH, $R^4$ = R, $R^5$ = OH, $R^6$ = H |
| Analog (101) | $R^1$ = NH, $R^2$ = OCOR, $R^3$ = OCOR, $R^4$ = R, $R^5$ = OH, $R^6$ = H |
| Analog (102) | $R^1$ = NH, $R^2$ = OZ, $R^3$ = OZ, $R^4$ = R, $R^5$ = OH, $R^6$ = H |
| Analog (103) | $R^1$ = NH, $R^2$ = OCOR, $R^3$ = OCOR, $R^4$ = R, $R^5$ = OCOR, $R^6$ = H |
| Analog (104) | $R^1$ = NH, $R^2$ = OZ, $R^3$ = OZ, $R^4$ = R, $R^5$ = OZ, $R^6$ = H |
| Analog (105) | $R^1$ = O, $R^2$ = OCOR, $R^3$ = OCOR, $R^4$ = R, $R^5$ = $OH_2$, $R^6$ = H |
| Analog (106) | $R^1$ = O, $R^2$ = OZ, $R^3$ = OZ, $R^4$ = R, $R^5$ = $OH_2$, $R^6$ = H |
| Analog (107) | $R^1$ = O, $R^2$ = OCOR, $R^3$ = OCOR, $R^4$ = R, $R^5$ = OCOR, $R^6$ = H |
| Analog (108) | $R^1$ = O, $R^2$ = OZ, $R^3$ = OZ, $R^4$ = R, $R^5$ = OZ, $R^6$ = H |
| Analog (109) | $R^1$ = NH, $R^2$ = OCOR, $R^3$ = OH, $R^4$ = H, $R^5$ = OH, $R^6$ = H |
| Analog (110) | $R^1$ = NH, $R^2$ = OZ, $R^3$ = OH, $R^4$ = H, $R^5$ = OH, $R^6$ = H |
| Analog (111) | $R^1$ = O, $R^2$ = OCOR, $R^3$ = OH, $R^4$ = H, $R^5$ = OH, $R^6$ = H |
| Analog (112) | $R^1$ = O, $R^2$ = OZ, $R^3$ = OH, $R^4$ = H, $R^5$ = OH, $R^6$ = H |
| Analog (113) | $R^1$ = NH, $R^2$ = OH, $R^3$ = OCOR, $R^4$ = R, $R^5$ = OH, $R^6$ = H |
| Analog (114) | $R^1$ = NH, $R^2$ = OH, $R^3$ = OZ, $R^4$ = R, $R^5$ = OH, $R^6$ = H |
| Analog (115) | $R^1$ = O, $R^2$ = OH, $R^3$ = OCOR, $R^4$ = R, $R^5$ = OH, $R^6$ = H |
| Analog (116) | $R^1$ = O, $R^2$ = OH, $R^3$ = OZ, $R^4$ = R, $R^5$ = OH, $R^6$ = H. |

30. A method for inhibiting a caspase wherein said method comprises administering to said caspase a caspase inhibiting amount of a compound having the following structure:

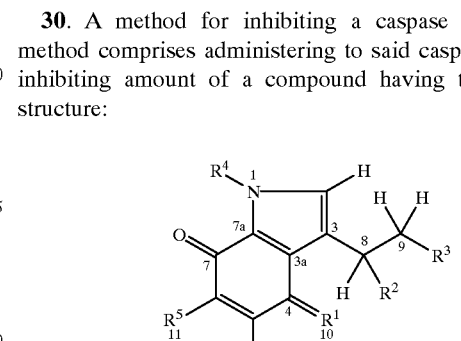

wherein $R^1$ is NH or O;
$R^2$ is OZ;
$R^3$ is OZ;
$R^4$ is H or R;

$R^5$ is $NH_2$, $NR_2$, or OZ; and
$R^6$ is H or X;
wherein Z is selected from the group consisting of H, R, COR, mesyl, tosyl, glutamyl, succinyl, and malonyl;
R is selected from the group consisting of C1 to C8 alkyl, phenyl, and benzyl; and
X is Cl, Br, or I.

31. The method, according to claim 30, wherein $R^1$ NH; $R^2$ is OH; $R^3$ is OH; $R^4$ is H; $R^5$ is $NH_2$ and $R^6$ is Cl.

32. The method, according to claim 30, wherein $R^1$ NH; $R^2$ is OCOR; $R^3$ is OCOR; $R^4$ is H; $R^5$ is $NH_2$; and $R^6$ is Cl.

33. The method, according to claim 30, wherein $R^1$ is O; $R^2$ is OH; $R^3$ is OH; $R^4$ is H; $R^5$ is $NH_2$; and $R^6$ is Cl.

34. The method, according to claim 30, wherein $R^1$ is O; $R^2$ is OCOR; $R^3$ is OCOR; $R^4$ is H; $R^5$ is $NH_2$; and $R^6$ is Cl.

35. The method, according to claim 30, wherein said compound is selected from the group consisting of:

| | |
|---|---|
| Analog (5) | $R^1$ = NH, $R^2$ = OH, $R^3$ = OCOR, $R^4$ = H, $R^5$ = $NH_2$, $R^6$ = X |
| Analog (6) | $R^1$ = NH, $R^2$ = OH, $R^3$ = OZ, $R^4$ = H, $R^5$ = $NH_2$, $R^6$ = X |
| Analog (7) | $R^1$ = NH, $R^2$ = OCOR, $R^3$ = OH, $R^4$ = H, $R^5$ = $NH_2$, $R^6$ = X |
| Analog (8) | $R^1$ = NH, $R^2$ = OZ, $R^3$ = OH, $R^4$ = H, $R^5$ = $NH_2$, $R^6$ = X |
| Analog (9) | $R^1$ = O, $R^2$ = OH, $R^3$ = OCOR, $R^4$ = H, $R^5$ = $NH_2$, $R^6$ = X |
| Analog (10) | $R^1$ = O, $R^2$ = OH, $R^3$ = OZ, $R^4$ = H, $R^5$ = $NH_2$, $R^6$ = X |
| Analog (11) | $R^1$ = O, $R^2$ = OCOR, $R^3$ = OH, $R^4$ = H, $R^5$ = $NH_2$, $R^6$ = X |
| Analog (12) | $R^1$ = O, $R^2$ = OZ, $R^3$ = OH, $R^4$ = H, $R^5$ = $NH_2$, $R^6$ = X |
| Analog (13) | $R^1$ = NH, $R^2$ = OH, $R^3$ = OH, $R^4$ = R, $R^5$ = $NH_2$, $R^6$ = X |
| Analog (14) | $R^1$ = O, $R^2$ = OH, $R^3$ = OH, $R^4$ = R, $R^5$ = $NH_2$, $R^6$ = X |
| Analog (15) | $R^1$ = NH, $R^2$ = OH, $R^3$ = OH, $R^4$ = H, $R^5$ = $NR_2$, $R^6$ = X |
| Analog (16) | $R^1$ = O, $R^2$ = OH, $R^3$ = OH, $R^4$ = H, $R^5$ = $NR_2$, $R^6$ = X |
| Analog (17) | $R^1$ = NH, $R^2$ = OH, $R^3$ = OH, $R^4$ = R, $R^5$ = $NR_2$, $R^6$ = X |
| Analog (18) | $R^1$ = O, $R^2$ = OH, $R^3$ = OH, $R^4$ = R, $R^5$ = $NR_2$, $R^6$ = X |
| Analog (19) | $R^1$ = NH, $R^2$ = OCOR, $R^3$ = OCOR, $R^4$ = R, $R^5$ = $NH_2$, $R^6$ = X |
| Analog (20) | $R^1$ = NH, $R^2$ = OZ, $R^3$ = OZ, $R^4$ = R, $R^5$ = $NH_2$, $R^6$ = X |
| Analog (21) | $R^1$ = O, $R^2$ = OCOR, $R^3$ = OCOR, $R^4$ = R, $R^5$ = $NH_2$, $R^6$ = X |
| Analog (22) | $R^1$ = O, $R^2$ = OZ, $R^3$ = OZ, $R^4$ = R, $R^5$ = $NH_2$, $R^6$ = X |
| Analog (23) | $R^1$ = NH, $R^2$ = OCOR, $R^3$ = OH, $R^4$ = H, $R^5$ = $NR_2$, $R^6$ = X |
| Analog (24) | $R^1$ = NH, $R^2$ = OZ, $R^3$ = OH, $R^4$ = H, $R^5$ = $NR_2$, $R^6$ = X |
| Analog (25) | $R^1$ = O, $R^2$ = OCOR, $R^3$ = OH, $R^4$ = H, $R^5$ = $NR_2$, $R^6$ = X |
| Analog (26) | $R^1$ = O, $R^2$ = OZ, $R^3$ = OH, $R^4$ = H, $R^5$ = $NR_2$, $R^6$ = X |
| Analog (27) | $R^1$ = NH, $R^2$ = OH, $R^3$ = OCOR, $R^4$ = R, $R^5$ = $NR_2$, $R^6$ = X |
| Analog (28) | $R^1$ = NH, $R^2$ = OH, $R^3$ = OZ, $R^4$ = R, $R^5$ = $NR_2$, $R^6$ = X |
| Analog (29) | $R^1$ = O, $R^2$ = OH, $R^3$ = OCOR, $R^4$ = R, $R^5$ = $NR_2$, $R^6$ = X |
| Analog (30) | $R^1$ = O, $R^2$ = OH, $R^3$ = OZ, $R^4$ = R, $R^5$ = $NR_2$, $R^6$ = X |
| Analog (31) | $R^1$ = NH, $R^2$ = OCOR, $R^3$ = OCOR, $R^4$ = H, $R^5$ = $NH_2$, $R^6$ = H |
| Analog (32) | $R^1$ = NH, $R^2$ = OZ, $R^3$ = OZ, $R^4$ = H, $R^5$ = $NH_2$, $R^6$ = H |
| Analog (33) | $R^1$ = O, $R^2$ = OCOR, $R^3$ = OCOR, $R^4$ = H; $R^5$ = $NH_2$, $R^6$ = H |
| Analog (34) | $R^1$ = O, $R^2$ = OZ, $R^3$ = OZ, $R^4$ = H, $R^5$ = $NH_2$, $R^6$ = H |
| Analog (35) | $R^1$ = NH, $R^2$ = OH, $R^3$ = OCOR, $R^4$ = H, $R^5$ = $NH_2$, $R^6$ = H |
| Analog (36) | $R^1$ = NH, $R^2$ = OH, $R^3$ = OZ, $R^4$ = H, $R^5$ = $NH_2$, $R^6$ = H |
| Analog (37) | $R^1$ = NH, $R^2$ = OCOR, $R^3$ = OH, $R^4$ = H, $R^5$ = $NH_2$, $R^6$ = H |
| Analog (38) | $R^1$ = NH, $R^2$ = OZ, $R^3$ = OH, $R^4$ = H, $R^5$ = $NH_2$, $R^6$ = H |
| Analog (39) | $R^1$ = O, $R^2$ = OH, $R^3$ = OCOR, $R^4$ = H, $R^5$ = $NH_2$, $R^6$ = H |
| Analog (40) | $R^1$ = O, $R^2$ = OH, $R^3$ = OZ, $R^4$ = H, $R^5$ = $NH_2$, $R^6$ = H |
| Analog (41) | $R^1$ = O, $R^2$ = OCOR, $R^3$ = OH, $R^4$ = H, $R^5$ = $NH_2$, $R^6$ = H |
| Analog (42) | $R^1$ = O, $R^2$ = OZ, $R^3$ = OH, $R^4$ = H, $R^5$ = $NH_2$, $R^6$ = H |
| Analog (43) | $R^1$ = NH, $R^2$ = OH, $R^3$ = OH, $R^4$ = R, $R^5$ = $NH_2$, $R^6$ = H |
| Analog (44) | $R^1$ = O, $R^2$ = OH, $R^3$ = OH, $R^4$ = R, $R^5$ = $NH_2$, $R^6$ = H |
| Analog (45) | $R^1$ = NH, $R^2$ = OH, $R^3$ = OH, $R^4$ = H, $R^5$ = $NR_2$, $R^6$ = H |
| Analog (46) | $R^1$ = O, $R^2$ = OH, $R^3$ = OH, $R^4$ = H, $R^5$ = $NR_2$, $R^6$ = H |
| Analog (47) | $R^1$ = NH, $R^2$ = OH, $R^3$ = OH, $R^4$ = R, $R^5$ = $NR_2$, $R^6$ = H |
| Analog (48) | $R^1$ = O, $R^2$ = OH, $R^3$ = OH, $R^4$ = R, $R^5$ = $NR_2$, $R^6$ = H |
| Analog (49) | $R^1$ = NH, $R^2$ = OCOR, $R^3$ = OCOR, $R^4$ = R, $R^5$ = $NH_2$, $R^6$ = H |
| Analog (50) | $R^1$ = NH, $R^2$ = OZ, $R^3$ = OZ, $R^4$ = R, $R^5$ = $NH_2$, $R^6$ = H |
| Analog (51) | $R^1$ = O, $R^2$ = OCOR, $R^3$ = OCOR, $R^4$ = R, $R^5$ = $NH_2$, $R^6$ = H |
| Analog (52) | $R^1$ = O, $R^2$ = OZ, $R^3$ = OZ, $R^4$ = R, $R^5$ = $NH_2$, $R^6$ = H |
| Analog (53) | $R^1$ = NH, $R^2$ = OCOR, $R^3$ = OH, $R^4$ = H, $R^5$ = $NR_2$, $R^6$ = H |
| Analog (54) | $R^1$ = NH, $R^2$ = OZ, $R^3$ = OH, $R^4$ = H, $R^5$ = $NR_2$, $R^6$ = H |
| Analog (55) | $R^1$ = O, $R^2$ = OCOR, $R^3$ = OH, $R^4$ = H, $R^5$ = $NR_2$, $R^6$ = H |
| Analog (56) | $R^1$ = O, $R^2$ = OZ, $R^3$ = OH, $R^4$ = H, $R^5$ = $NR_2$, $R^6$ = H |
| Analog (57) | $R^1$ = NH, $R^2$ = OH, $R^3$ = OCOR, $R^4$ = R, $R^5$ = $NR_2$, $R^6$ = H |
| Analog (58) | $R^1$ = NH, $R^2$ = OH, $R^3$ = OZ, $R^4$ = R, $R^5$ = $NR_2$, $R^6$ = H |
| Analog (59) | $R^1$ = O, $R^2$ = OH, $R^3$ = OCOR, $R^4$ = R, $R^5$ = $NR_2$, $R^6$ = H |
| Analog (60) | $R^1$ = O, $R^2$ = OH, $R^3$ = OZ, $R^4$ = R, $R^5$ = $NR_2$, $R^6$ = H |
| Analog (61) | $R^1$ = NH, $R^2$ = OCOR, $R^3$ = OCOR, $R^4$ = H, $R^5$ = OH, $R^6$ = X |
| Analog (62) | $R^1$ = NH, $R^2$ = OZ, $R^3$ = OZ, $R^4$ = H, $R^5$ = OH, $R^6$ = X |
| Analog (63) | $R^1$ = NH, $R^2$ = OCOR, $R^3$ = OCOR, $R^4$ = H, $R^5$ = OCOR, $R^6$ = X |
| Analog (64) | $R^1$ = NH, $R^2$ = OZ, $R^3$ = OZ, $R^4$ = H, $R^5$ = OZ, $R^6$ = X |
| Analog (65) | $R^1$ = O, $R^2$ = OCOR, $R^3$ = OCOR, $R^4$ = H, $R^5$ = OH, $R^6$ = X |
| Analog (66) | $R^1$ = O, $R^2$ = OZ, $R^3$ = OZ, $R^4$ = H, $R^5$ = OH, $R^6$ = X |
| Analog (67) | $R^1$ = O, $R^2$ = OCOR, $R^3$ = OCOR, $R^4$ = H, $R^5$ = OCOR, $R^6$ = X |
| Analog (68) | $R^1$ = O, $R^2$ = OZ, $R^3$ = OZ, $R^4$ = H, $R^5$ = OZ, $R^6$ = X |
| Analog (69) | $R^1$ = NH, $R^2$ = OH, $R^3$ = OH, $R^4$ = H, $R^5$ = OH, $R^6$ = X |
| Analog (70) | $R^1$ = O, $R^2$ = OH, $R^3$ = OH, $R^4$ = H, $R^5$ = OH, $R^6$ = X |
| Analog (71) | $R^1$ = NH, $R^2$ = OH, $R^3$ = OH, $R^4$ = R, $R^5$ = OH, $R^6$ = X |
| Analog (72) | $R^1$ = O, $R^2$ = OH, $R^3$ = OH, $R^4$ = R, $R^5$ = OH, $R^6$ = X |
| Analog (73) | $R^1$ = NH, $R^2$ = OCOR, $R^3$ = OCOR, $R^4$ = R, $R^5$ = OH, $R^6$ = X |
| Analog (74) | $R^1$ = NH, $R^2$ = OZ, $R^3$ = OZ, $R^4$ = R, $R^5$ = OH, $R^6$ = X |
| Analog (75) | $R^1$ = NH, $R^2$ = OCOR, $R^3$ = OCOR, $R^4$ = R, $R^5$ = OCOR, $R^6$ = X |
| Analog (76) | $R^1$ = NH, $R^2$ = OZ, $R^3$ = OZ, $R^4$ = R, $R^5$ = OZ, $R^6$ = X |
| Analog (77) | $R^1$ = O, $R^2$ = OCOR, $R^3$ = OCOR, $R^4$ = R, $R^5$ = $OH_2$, $R^6$ = X |
| Analog (78) | $R^1$ = O, $R^2$ = OZ, $R^3$ = OZ, $R^4$ = R, $R^5$ = $OH_2$, $R^6$ = X |
| Analog (79) | $R^1$ = O, $R^2$ = OCOR, $R^3$ = OCOR, $R^4$ = R, $R^5$ = OCOR, $R^6$ = X |
| Analog (80) | $R^1$ = O, $R^2$ = OZ, $R^3$ = OZ, $R^4$ = R, $R^5$ = OZ, $R^6$ = X |
| Analog (81) | $R^1$ = NH, $R^2$ = OCOR, $R^3$ = OH, $R^4$ = H, $R^5$ = OH, $R^6$ = X |
| Analog (82) | $R^1$ = NH, $R^2$ = OZ, $R^3$ = OH, $R^4$ = H, $R^5$ = OH, $R^6$ = X |
| Analog (83) | $R^1$ = O, $R^2$ = OCOR, $R^3$ = OH, $R^4$ = H, $R^5$ = OH, $R^6$ = X |
| Analog (84) | $R^1$ = O, $R^2$ = OZ, $R^3$ = OH, $R^4$ = H, $R^5$ = OH, $R^6$ = X |
| Analog (85) | $R^1$ = NH, $R^2$ = OH, $R^3$ = OCOR, $R^4$ = R, $R^5$ = OH, $R^6$ = X |
| Analog (86) | $R^1$ = NH, $R^2$ = OH, $R^3$ = OZ, $R^4$ = R, $R^5$ = OH, $R^6$ = X |
| Analog (87) | $R^1$ = O, $R^2$ = OH, $R^3$ = OCOR, $R^4$ = R, $R^5$ = OH, $R^6$ = X |
| Analog (88) | $R^1$ = O, $R^2$ = OH, $R^3$ = OZ, $R^4$ = R, $R^5$ = OH, $R^6$ = X |
| Analog (89) | $R^1$ = NH, $R^2$ = OCOR, $R^3$ = OCOR, $R^4$ = H, $R^5$ = OH, $R^6$ = H |
| Analog (90) | $R^1$ = NH, $R^2$ = OZ, $R^3$ = OZ, $R^4$ = H, $R^5$ = OH, $R^6$ = H |
| Analog (91) | $R^1$ = NH, $R^2$ = OCOR, $R^3$ = OCOR, $R^4$ = H, $R^5$ = OCOR, $R^6$ = H |
| Analog (92) | $R^1$ = NH, $R^2$ = OZ, $R^3$ = OZ, $R^4$ = H, $R^5$ = OZ, $R^6$ = H |
| Analog (93) | $R^1$ = O, $R^2$ = OCOR, $R^3$ = OCOR, $R^4$ = H, $R^5$ = OH, $R^6$ = H |
| Analog (94) | $R^1$ = O, $R^2$ = OZ, $R^3$ = OZ, $R^4$ = H, $R^5$ = OH, $R^6$ = H |
| Analog (95) | $R^1$ = O, $R^2$ = OCOR, $R^3$ = OCOR, $R^4$ = H, $R^5$ = OCOR, $R^6$ = H |
| Analog (96) | $R^1$ = O, $R^2$ = OZ, $R^3$ = OZ, $R^4$ = H, $R^5$ = OZ, $R^6$ = H |
| Analog (97) | $R^1$ = NH, $R^2$ = OH, $R^3$ = OH, $R^4$ = H, $R^5$ = OH, $R^6$ = H |
| Analog (98) | $R^1$ = O, $R^2$ = OH, $R^3$ = OH, $R^4$ = H, $R^5$ = OH, $R^6$ = H |
| Analog (99) | $R^1$ = NH, $R^2$ = OH, $R^3$ = OH, $R^4$ = R, $R^5$ = OH, $R^6$ = H |
| Analog (100) | $R^1$ = O, $R^2$ = OH, $R^3$ = OH, $R^4$ = R, $R^5$ = OH, $R^6$ = H |
| Analog (101) | $R^1$ = NH, $R^2$ = OCOR, $R^3$ = OCOR, $R^4$ = R, $R^5$ = OH, $R^6$ = H |
| Analog (102) | $R^1$ = NH, $R^2$ = OZ, $R^3$ = OZ, $R^4$ = R, $R^5$ = OH, $R^6$ = H |
| Analog (103) | $R^1$ = NH, $R^2$ = OCOR, $R^3$ = OCOR, $R^4$ = R, $R^5$ = OCOR, $R^6$ = H |
| Analog (104) | $R^1$ = NH, $R^2$ = OZ, $R^3$ = OZ, $R^4$ = R, $R^5$ = OZ, $R^6$ = H |
| Analog (105) | $R^1$ = O, $R^2$ = OCOR, $R^3$ = OCOR, $R^4$ = R, $R^5$ = $OH_2$, $R^6$ = H |
| Analog (106) | $R^1$ = O, $R^2$ = OZ, $R^3$ = OZ, $R^4$ = R, $R^5$ = $OH_2$, $R^6$ = H |
| Analog (107) | $R^1$ = O, $R^2$ = OCOR, $R^3$ = OCOR, $R^4$ = R, $R^5$ = OCOR, $R^6$ = H |
| Analog (108) | $R^1$ = O, $R^2$ = OZ, $R^3$ = OZ, $R^4$ = R, $R^5$ = OZ, $R^6$ = H |

| | |
|---|---|
| Analog (109) | $R^1$ = NH, $R^2$ = OCOR, $R^3$ = OH, $R^4$ = H, $R^5$ = OH, $R^6$ = H |
| Analog (110) | $R^1$ = NH, $R^2$ = OZ, $R^3$ = OH, $R^4$ = H, $R^5$ = OH, $R^6$ = H |
| Analog (111) | $R^1$ = O, $R^2$ = OCOR, $R^3$ = OH, $R^4$ = H, $R^5$ = OH, $R^6$ = H |
| Analog (112) | $R^1$ = O, $R^2$ = OZ, $R^3$ = OH, $R^4$ = H, $R^5$ = OH, $R^6$ = H |
| Analog (113) | $R^1$ = NH, $R^2$ = OH, $R^3$ = OCOR, $R^4$ = R, $R^5$ = OH, $R^6$ = H |
| Analog (114) | $R^1$ = NH, $R^2$ = OH, $R^3$ = OZ, $R^4$ = R, $R^5$ = OH, $R^6$ = H |
| Analog (115) | $R^1$ = O, $R^2$ = OH, $R^3$ = OCOR, $R^4$ = R, $R^5$ = OH, $R^6$ = H |
| Analog (116) | $R^1$ = O, $R^2$ = OH, $R^3$ = OZ, $R^4$ = R, $R^5$ = OH, $R^6$ = H. |

36. The method, according to claim 30, which is used to treat an animal suffering from a neurodegenerative disorder.

37. The method, according to claim 36, wherein said neurodegenerative disorder is selected from the group consisting of ALS and Alzheimer's disease.

38. A method for inhibiting calcineurin activity in an animal wherein said method comprises administering to said animal a calcineurin inhibiting amount of a compound having the following structure:

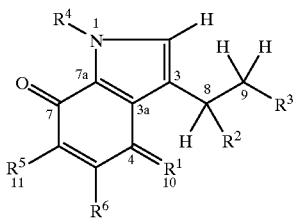

wherein $R^1$ is NH or O;
$R^2$ is OZ;
$R^3$ is OZ;
$R^4$ is be H or R;
$R^5$ is $NH_2$, $NR_2$, or OZ; and
$R^6$ is H or X;
wherein Z is selected from the group consisting of H, R, COR, mesyl, tosyl, glutamyl, succinyl, and malonyl;
R is selected from the group consisting of C1 to C8 alkyl, phenyl, and benzyl; and
X is Cl, Br, or I.

39. The method, according to claim 38, wherein $R^1$ NH; $R^2$ is OH; $R^3$ is OH; $R^4$ is H; $R^5$ is $NH_2$ and $R^6$ is Cl.

40. The method, according to claim 38, wherein $R^1$ NH; $R^2$ is OCOR; $R^3$ is OCOR; $R^4$ is H; $R^5$ is $NH_2$; and $R^6$ is Cl.

41. The method, according to claim 38, wherein $R^1$ is O; $R^2$ is OH; $R^3$ is OH; $R^4$ is H; $R^5$ is $NH_2$; and $R^6$ is Cl.

42. The method, according to claim 38, wherein $R^1$ is O; $R^2$ is OCOR; $R^3$ is OCOR; $R^4$ is H; $R^5$ is $NH_2$; and R is Cl.

43. The method, according to claim 38, wherein said compound is selected from the group consisting of:

| | |
|---|---|
| Analog (5) | $R^1$ = NH, $R^2$ = OH, $R^3$ = OCOR, $R^4$ = H, $R^5$ = $NH_2$, $R^6$ = X |
| Analog (6) | $R^1$ = NH, $R^2$ = OH, $R^3$ = OZ, $R^4$ = H, $R^5$ = $NH_2$, $R^6$ = X |
| Analog (7) | $R^1$ = NH, $R^2$ = OCOR, $R^3$ = OH, $R^4$ = H, $R^5$ = $NH_2$, $R^6$ = X |
| Analog (8) | $R^1$ = NH, $R^2$ = OZ, $R^3$ = OH, $R^4$ = H, $R^5$ = $NH_2$, $R^6$ = X |
| Analog (9) | $R^1$ = O, $R^2$ = OH, $R^3$ = OCOR, $R^4$ = H, $R^5$ = $NH_2$, $R^6$ = X |
| Analog (10) | $R^1$ = O, $R^2$ = OH, $R^3$ = OZ, $R^4$ = H, $R^5$ = $NH_2$, $R^6$ = X |
| Analog (11) | $R^1$ = O, $R^2$ = OCOR, $R^3$ = OH, $R^4$ = H, $R^5$ = $NH_2$, $R^6$ = X |
| Analog (12) | $R^1$ = O, $R^2$ = OZ, $R^3$ = OH, $R^4$ = H, $R^5$ = $NH_2$, $R^6$ = X |
| Analog (13) | $R^1$ = NH, $R^2$ = OH, $R^3$ = OH, $R^4$ = R, $R^5$ = $NH_2$, $R^6$ = X |
| Analog (14) | $R^1$ = O, $R^2$ = OH, $R^3$ = OH, $R^4$ = R, $R^5$ = $NH_2$, $R^6$ = X |
| Analog (15) | $R^1$ = NH, $R^2$ = OH, $R^3$ = OH, $R^4$ = H, $R^5$ = $NR_2$, $R^6$ = X |
| Analog (16) | $R^1$ = O, $R^2$ = OH, $R^3$ = OH, $R^4$ = H, $R^5$ = $NR_2$, $R^6$ = X |
| Analog (17) | $R^1$ = NH, $R^2$ = OH, $R^3$ = OH, $R^4$ = R, $R^5$ = $NR_2$, $R^6$ = X |
| Analog (18) | $R^1$ = O, $R^2$ = OH, $R^3$ = OH, $R^4$ = R, $R^5$ = $NR_2$, $R^6$ = X |
| Analog (19) | $R^1$ = NH, $R^2$ = OCOR, $R^3$ = OCOR, $R^4$ = R, $R^5$ = $NH_2$, $R^6$ = X |
| Analog (20) | $R^1$ = NH, $R^2$ = OZ, $R^3$ = OZ, $R^4$ = R, $R^5$ = $NH_2$, $R^6$ = X |
| Analog (21) | $R^1$ = O, $R^2$ = OCOR, $R^3$ = OCOR, $R^4$ = R, $R^5$ = $NH_2$, $R^6$ = X |
| Analog (22) | $R^1$ = O, $R^2$ = OZ, $R^3$ = OZ, $R^4$ = R, $R^5$ = $NH_2$, $R^6$ = X |
| Analog (23) | $R^1$ = NH, $R^2$ = OCOR, $R^3$ = OH, $R^4$ = H, $R^5$ = $NR_2$, $R^6$ = X |
| Analog (24) | $R^1$ = NH, $R^2$ = OZ, $R^3$ = OH, $R^4$ = H, $R^5$ = $NR_2$, $R^6$ = X |
| Analog (25) | $R^1$ = O, $R^2$ = OCOR, $R^3$ = OH, $R^4$ = H, $R^5$ = $NR_2$, $R^6$ = X |
| Analog (26) | $R^1$ = O, $R^2$ = OZ, $R^3$ = OH, $R^4$ = H, $R^5$ = $NR_2$, $R^6$ = X |
| Analog (27) | $R^1$ = NH, $R^2$ = OH, $R^3$ = OCOR, $R^4$ = R, $R^5$ = $NR_2$, $R^6$ = X |
| Analog (28) | $R^1$ = NH, $R^2$ = OH, $R^3$ = OZ, $R^4$ = R, $R^5$ = $NR_2$, $R^6$ = X |
| Analog (29) | $R^1$ = O, $R^2$ = OH, $R^3$ = OCOR, $R^4$ = R, $R^5$ = $NR_2$, $R^6$ = X |
| Analog (30) | $R^1$ = O, $R^2$ = OH, $R^3$ = OZ, $R^4$ = R, $R^5$ = $NR_2$, $R^6$ = X |
| Analog (31) | $R^1$ = NH, $R^2$ = OCOR, $R^3$ = OCOR, $R^4$ = H, $R^5$ = $NH_2$, $R^6$ = H |
| Analog (32) | $R^1$ = NH, $R^2$ = OZ, $R^3$ = OZ, $R^4$ = H, $R^5$ = $NH_2$, $R^6$ = H |
| Analog (33) | $R^1$ = O, $R^2$ = OCOR, $R^3$ = OCOR, $R^4$ = H; $R^5$ = $NH_2$, $R^6$ = H |
| Analog (34) | $R^1$ = O, $R^2$ = OZ, $R^3$ = OZ, $R^4$ = H, $R^5$ = $NH_2$, $R^6$ = H |
| Analog (35) | $R^1$ = NH, $R^2$ = OH, $R^3$ = OCOR, $R^4$ = H, $R^5$ = $NH_2$, $R^6$ = H |
| Analog (36) | $R^1$ = NH, $R^2$ = OH, $R^3$ = OZ, $R^4$ = H, $R^5$ = $NH_2$, $R^6$ = H |
| Analog (37) | $R^1$ = NH, $R^2$ = OCOR, $R^3$ = OH, $R^4$ = H, $R^5$ = $NH_2$, $R^6$ = H |
| Analog (38) | $R^1$ = NH, $R^2$ = OZ, $R^3$ = OH, $R^4$ = H, $R^5$ = $NH_2$, $R^6$ = H |
| Analog (39) | $R^1$ = O, $R^2$ = OH, $R^3$ = OCOR, $R^4$ = H, $R^5$ = $NH_2$, $R^6$ = H |
| Analog (40) | $R^1$ = O, $R^2$ = OH, $R^3$ = OZ, $R^4$ = H, $R^5$ = $NH_2$, $R^6$ = H |
| Analog (41) | $R^1$ = O, $R^2$ = OCOR, $R^3$ = OH, $R^4$ = H, $R^5$ = $NH_2$, $R^6$ = H |
| Analog (42) | $R^1$ = O, $R^2$ = OZ, $R^3$ = OH, $R^4$ = H, $R^5$ = $NH_2$, $R^6$ = H |
| Analog (43) | $R^1$ = NH, $R^2$ = OH, $R^3$ = OH, $R^4$ = R, $R^5$ = $NH_2$, $R^6$ = H |
| Analog (44) | $R^1$ = O, $R^2$ = OH, $R^3$ = OH, $R^4$ = R, $R^5$ = $NH_2$, $R^6$ = H |
| Analog (45) | $R^1$ = NH, $R^2$ = OH, $R^3$ = OH, $R^4$ = H, $R^5$ = $NR_2$, $R^6$ = H |
| Analog (46) | $R^1$ = O, $R^2$ = OH, $R^3$ = OH, $R^4$ = H, $R^5$ = $NR_2$, $R^6$ = H |
| Analog (47) | $R^1$ = NH, $R^2$ = OH, $R^3$ = OH, $R^4$ = R, $R^5$ = $NR_2$, $R^6$ = H |
| Analog (48) | $R^1$ = O, $R^2$ = OH, $R^3$ = OH, $R^4$ = R, $R^5$ = $NR_2$, $R^6$ = H |
| Analog (49) | $R^1$ = NH, $R^2$ = OCOR, $R^3$ = OCOR, $R^4$ = R, $R^5$ = $NH_2$, $R^6$ = H |
| Analog (50) | $R^1$ = NH, $R^2$ = OZ, $R^3$ = OZ, $R^4$ = R, $R^5$ = $NH_2$, $R^6$ = H |
| Analog (51) | $R^1$ = O, $R^2$ = OCOR, $R^3$ = OCOR, $R^4$ = R, $R^5$ = $NH_2$, $R^6$ = H |
| Analog (52) | $R^1$ = O, $R^2$ = OZ, $R^3$ = OZ, $R^4$ = R, $R^5$ = $NH_2$, $R^6$ = H |
| Analog (53) | $R^1$ = NH, $R^2$ = OCOR, $R^3$ = OH, $R^4$ = H, $R^5$ = $NR_2$, $R^6$ = H |
| Analog (54) | $R^1$ = NH, $R^2$ = OZ, $R^3$ = OH, $R^4$ = H, $R^5$ = $NR_2$, $R^6$ = H |
| Analog (55) | $R^1$ = O, $R^2$ = OCOR, $R^3$ = OH, $R^4$ = H, $R^5$ = $NR_2$, $R^6$ = H |
| Analog (56) | $R^1$ = O, $R^2$ = OZ, $R^3$ = OH, $R^4$ = H, $R^5$ = $NR_2$, $R^6$ = H |
| Analog (57) | $R^1$ = NH, $R^2$ = OH, $R^3$ = OCOR, $R^4$ = R, $R^5$ = $NR_2$, $R^6$ = H |
| Analog (58) | $R^1$ = NH, $R^2$ = OH, $R^3$ = OZ, $R^4$ = R, $R^5$ = $NR_2$, $R^6$ = H |
| Analog (59) | $R^1$ = O, $R^2$ = OH, $R^3$ = OCOR, $R^4$ = R, $R^5$ = $NR_2$, $R^6$ = H |
| Analog (60) | $R^1$ = O, $R^2$ = OH, $R^3$ = OZ, $R^4$ = R, $R^5$ = $NR_2$, $R^6$ = H |
| Analog (61) | $R^1$ = NH, $R^2$ = OCOR, $R^3$ = OCOR, $R^4$ = H, $R^5$ = OH, $R^6$ = X |
| Analog (62) | $R^1$ = NH, $R^2$ = OZ, $R^3$ = OZ, $R^4$ = H, $R^5$ = OH, $R^6$ = X |
| Analog (63) | $R^1$ = NH, $R^2$ = OCOR, $R^3$ = OCOR, $R^4$ = H, $R^5$ = OCOR, $R^6$ = X |
| Analog (64) | $R^1$ = NH, $R^2$ = OZ, $R^3$ = OZ, $R^4$ = H, $R^5$ = OZ, $R^6$ = X |
| Analog (65) | $R^1$ = O, $R^2$ = OCOR, $R^3$ = OCOR, $R^4$ = H, $R^5$ = OH, $R^6$ = X |
| Analog (66) | $R^1$ = O, $R^2$ = OZ, $R^3$ = OZ, $R^4$ = H, $R^5$ = OH, $R^6$ = X |
| Analog (67) | $R^1$ = O, $R^2$ = OCOR, $R^3$ = OCOR, $R^4$ = H, $R^5$ = OCOR, $R^6$ = X |
| Analog (68) | $R^1$ = O, $R^2$-OZ, $R^3$ = OZ, $R^4$ = H, $R^5$ = OZ, $R^6$ = X |
| Analog (69) | $R^1$ = NH, $R^2$ = OH, $R^3$ = OH, $R^4$ = H, $R^5$ = OH, $R^6$ = X |
| Analog (70) | $R^1$ = O, $R^2$ = OH, $R^3$ = OH, $R^4$ = H, $R^5$ = OH, $R^6$ = X |
| Analog (71) | $R^1$ = NH, $R^2$ = OH, $R^3$ = OH, $R^4$ = R, $R^5$ = OH, $R^6$ = X |
| Analog (72) | $R^1$ = O, $R^2$ = OH, $R^3$ = OH, $R^4$ = R, $R^5$ = OH, $R^6$ = X |
| Analog (73) | $R^1$ = NH, $R^2$ = OCOR, $R^3$ = OCOR, $R^4$ = R, $R^5$ = OH, $R^6$ = X |
| Analog (74) | $R^1$ = NH, $R^2$ = OZ, $R^3$ = OZ, $R^4$ = R, $R^5$ = OH, $R^6$ = X |
| Analog (75) | $R^1$ = NH, $R^2$ = OCOR, $R^3$ = OCOR, $R^4$ = R, $R^5$ = OCOR, |

-continued

Analog (76) $R^1$ = NH, $R^2$ = OZ, $R^3$ = OZ, $R^4$ = R, $R^5$ = OZ, $R^6$ = X
Analog (77) $R^1$ = O, $R^2$ = OCOR, $R^3$ = OCOR, $R^4$ = R, $R^5$ = OH$_2$, $R^6$ = X
Analog (78) $R^1$ = O, $R^2$ = OZ, $R^3$ = OZ, $R^4$ = R, $R^5$ = OH$_2$, $R^6$ = X
Analog (79) $R^1$ = O, $R^2$ = OCOR, $R^3$ = OCOR, $R^4$ = R, $R^5$ = OCOR, $R^6$ = X
Analog (80) $R^1$ = O, $R^2$ = OZ, $R^3$ = OZ, $R^4$ = R, $R^5$ = OZ, $R^6$ = X
Analog (81) $R^1$ = NH, $R^2$ = OCOR, $R^3$ = OH, $R^4$ = H, $R^5$ = OH, $R^6$ = X
Analog (82) $R^1$ = NH, $R^2$ = OZ, $R^3$ = OH, $R^4$ = H, $R^5$ = OH, $R^6$ = X
Analog (83) $R^1$ = O, $R^2$ = OCOR, $R^3$ = OH, $R^4$ = H, $R^5$ = OH, $R^6$ = X
Analog (84) $R^1$ = O, $R^2$ = OZ, $R^3$ = OH, $R^4$ = H, $R^5$ = OH, $R^6$ = X
Analog (85) $R^1$ = NH, $R^2$ = OH, $R^3$ = OCOR, $R^4$ = R, $R^5$ = OH, $R^6$ = X
Analog (86) $R^1$ = NH, $R^2$ = OH, $R^3$ = OZ, $R^4$ = R, $R^5$ = OH, $R^6$ = X
Analog (87) $R^1$ = O, $R^2$ = OH, $R^3$ = OCOR, $R^4$ = R, $R^5$ = OH, $R^6$ = X
Analog (88) $R^1$ = O, $R^2$ = OH, $R^3$ = OZ, $R^4$ = R, $R^5$ = OH, $R^6$ = X
Analog (89) $R^1$ = NH, $R^2$ = OCOR, $R^3$ = OCOR, $R^4$ = H, $R^5$ = OH, $R^6$ = H
Analog (90) $R^1$ = NH, $R^2$ = OZ, $R^3$ = OZ, $R^4$ = H, $R^5$ = OH, $R^6$ = H
Analog (91) $R^1$ = NH, $R^2$ = OCOR, $R^3$ = OCOR, $R^4$ = H, $R^5$ = OCOR, $R^6$ = H
Analog (92) $R^1$ = NH, $R^2$ = OZ, $R^3$ = OZ, $R^4$ = H, $R^5$ = OZ, $R^6$ = H
Analog (93) $R^1$ = O, $R^2$ = OCOR, $R^3$ = OCOR, $R^4$ = H, $R^5$ = OH, $R^6$ = H
Analog (94) $R^1$ = O, $R^2$ = OZ, $R^3$ = OZ, $R^4$ = H, $R^5$ = OH, $R^6$ = H
Analog (95) $R^1$ = O, $R^2$ = OCOR, $R^3$ = OCOR, $R^4$ = H, $R^5$ = OCOR, $R^6$ = H
Analog (96) $R^1$ = O, $R^2$ = OZ, $R^3$ = OZ, $R^4$ = H, $R^5$ = OZ, $R^6$ = H
Analog (97) $R^1$ = NH, $R^2$ = OH, $R^3$ = OH, $R^4$ = H, $R^5$ = OH, $R^6$ = H
Analog (98) $R^1$ = O, $R^2$ = OH, $R^3$ = OH, $R^4$ = H, $R^5$ = OH, $R^6$ = H
Analog (99) $R^1$ = NH, $R^2$ = OH, $R^3$ = OH, $R^4$ = R, $R^5$ = OH, $R^6$ = H
Analog (100) $R^1$ = O, $R^2$ = OH, $R^3$ = OH, $R^4$ = R, $R^5$ = OH, $R^6$ = H
Analog (101) $R^1$ = NH, $R^2$ = OCOR, $R^3$ = OCOR, $R^4$ = R, $R^5$ = OH, $R^6$ = H
Analog (102) $R^1$ = NH, $R^2$ = OZ, $R^3$ = OZ, $R^4$ = R, $R^5$ = OH, $R^6$ = H
Analog (103) $R^1$ = NH, $R^2$ = OCOR, $R^3$ = OCOR, $R^4$ = R, $R^5$ = OCOR, $R^6$ = H
Analog (104) $R^1$ = NH, $R^2$ = OZ, $R^3$ = OZ, $R^4$ = R, $R^5$ = OZ, $R^6$ = H
Analog (105) $R^1$ = O, $R^2$ = OCOR, $R^3$ = OCOR, $R^4$ = R, $R^5$ = OH$_2$, $R^6$ = H
Analog (106) $R^1$ = O, $R^2$ = OZ, $R^3$ = OZ, $R^4$ = R, $R^5$ = OH$_2$, $R^6$ = H
Analog (107) $R^1$ = O, $R^2$ = OCOR, $R^3$ = OCOR, $R^4$ = R, $R^5$ = OCOR, $R^6$ = H
Analog (108) $R^1$ = O, $R^2$ = OZ, $R^3$ = OZ, $R^4$ = R, $R^5$ = OZ, $R^6$ = H
Analog (109) $R^1$ = NH, $R^2$ = OCOR, $R^3$ = OH, $R^4$ = H, $R^5$ = OH, $R^6$ = H
Analog (110) $R^1$ = NH, $R^2$ = OZ, $R^3$ = OH, $R^4$ = H, $R^5$ = OH, $R^6$ = H
Analog (111) $R^1$ = O, $R^2$ = OCOR, $R^3$ = OH, $R^4$ = H, $R^5$ = OH, $R^6$ = H
Analog (112) $R^1$ = O, $R^2$ = OZ, $R^3$ = OH, $R^4$ = H, $R^5$ = OH, $R^6$ = H
Analog (113) $R^1$ = NH, $R^2$ = OH, $R^3$ = OCOR, $R^4$ = R, $R^5$ = OH, $R^6$ = H
Analog (114) $R^1$ = NH, $R^2$ = OH, $R^3$ = OZ, $R^4$ = R, $R^5$ = OH, $R^6$ = H
Analog (115) $R^1$ = O, $R^2$ = OH, $R^3$ = OCOR, $R^4$ = R, $R^5$ = OH, $R^6$ = H
Analog (116) $R^1$ = O, $R^2$ = OH, $R^3$ = OZ, $R^4$ = R, $R^5$ = OH, $R^6$ = H.

* * * * *

UNITED STATES PATENT AND TRADEMARK OFFICE
CERTIFICATE OF CORRECTION

PATENT NO.   : 6,218,419 B1
DATED        : April 17, 2001
INVENTOR(S)  : Gunasekera et al.

It is certified that error appears in the above-identified patent and that said Letters Patent is hereby corrected as shown below:

Column 6,
Line 43, "diazotiation" should read -- diazotization --.

Column 31, claim 31,
Line 8, "$R^1$ NH;" should read -- $R^1$ is NH; --.

Column 31, claim 32,
Line 10, "$R^1$ NH;" should read -- $R^1$ is NH; --.

Column 33, claim 39,
Line 45, "$R^1$ NH;" should read -- $R^1$ is NH; --.

Column 33, claim 40,
Line 47, "$R^1$ NH;" should read -- $R^1$ is NH; --.

Column 33, claim 42,
Line 52, "R is Cl." should read -- $R^6$ is Cl. --

Signed and Sealed this

Twenty-sixth Day of February, 2002

Attest:

JAMES E. ROGAN
Attesting Officer    Director of the United States Patent and Trademark Office